(12) United States Patent
McFarland et al.

(10) Patent No.: US 11,890,620 B2
(45) Date of Patent: Feb. 6, 2024

(54) MINIATURIZED DNA MICROARRAY FOR SMALL-VOLUME SAMPLE PROCESSING

(71) Applicant: The Charles Stark Draper Laboratory, Inc., Cambridge, MA (US)

(72) Inventors: Kirsty A. McFarland, Melrose, MA (US); Charles A. Lissandrello, Newtonville, MA (US); Andrew P. Magyar, Arlington, MA (US); Erin Rosenberger, Quincy, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 719 days.

(21) Appl. No.: 16/755,505

(22) PCT Filed: Oct. 12, 2018

(86) PCT No.: PCT/US2018/055600
§ 371 (c)(1),
(2) Date: Apr. 10, 2020

(87) PCT Pub. No.: WO2019/075321
PCT Pub. Date: Apr. 18, 2019

(65) Prior Publication Data
US 2021/0220823 A1 Jul. 22, 2021

Related U.S. Application Data

(60) Provisional application No. 62/687,012, filed on Jun. 19, 2018, provisional application No. 62/572,264, filed on Oct. 13, 2017.

(51) Int. Cl.
*B01L 3/00* (2006.01)
*B01L 7/00* (2006.01)
(Continued)

(52) U.S. Cl.
CPC ..... *B01L 3/50853* (2013.01); *B01L 3/502715* (2013.01); *B01L 3/502746* (2013.01);
(Continued)

(58) Field of Classification Search
CPC .......... B01L 3/50853; B01L 3/502715; B01L 3/502746; B01L 7/00; B01L 2200/0689;
(Continued)

(56) References Cited

U.S. PATENT DOCUMENTS 8,592,221 B2  11/2013  Fraden et al.
9,068,699 B2   6/2015  Fraden et al.
(Continued)

FOREIGN PATENT DOCUMENTS

WO   WO 2002/072264 A1   9/2002
WO   WO 2004/087323 A1   10/2004
WO   WO 2010/111265 A1   9/2010

OTHER PUBLICATIONS

International Search Report and Written Opinion of the International Searching Authority, dated Feb. 27, 2019, from International Application No. PCT/US2018/055600, filed on Oct. 12, 2018. 20 pages.

(Continued)

*Primary Examiner* — Dennis White
(74) *Attorney, Agent, or Firm* — HoustonHogle LLP

(57) ABSTRACT

Miniaturized DNA microarrays are described to be used in conjunction with microfluidic channels or microcentrifuge tubes and microcentrifuge filters to reduce sample size, incubation time and to increase overall binding efficiency.

7 Claims, 24 Drawing Sheets
(1 of 24 Drawing Sheet(s) Filed in Color)

(51) Int. Cl.
  *B04B 3/00* (2006.01)
  *B04B 5/04* (2006.01)
  *C12Q 1/6837* (2018.01)
  *C12Q 1/6874* (2018.01)

(52) U.S. Cl.
  CPC .................. *B01L 7/00* (2013.01); *B04B 3/00* (2013.01); *B04B 5/0414* (2013.01); *C12Q 1/6837* (2013.01); *C12Q 1/6874* (2013.01); *B01L 2200/0689* (2013.01); *B01L 2200/16* (2013.01); *B01L 2300/044* (2013.01); *B01L 2300/0636* (2013.01); *B01L 2300/168* (2013.01)

(58) Field of Classification Search
  CPC ........... B01L 2200/16; B01L 2300/044; B01L 2300/0636; B01L 2300/168; B01L 2300/041; B01L 2300/0896; B04B 3/00; B04B 5/0414; C12Q 1/6837; C12Q 1/6874
  See application file for complete search history.

(56) References Cited

U.S. PATENT DOCUMENTS

| | | |
|---|---|---|
| 2004/0248287 A1* | 12/2004 | Hu .................... B01L 3/508 435/287.2 |
| 2005/0277125 A1 | 12/2005 | Benn et al. |
| 2009/0053732 A1 | 2/2009 | Vermesh et al. |
| 2010/0284859 A1 | 11/2010 | Cooney et al. |
| 2011/0143966 A1* | 6/2011 | McGall .................. C07F 7/188 546/14 |
| 2016/0114322 A1 | 4/2016 | Ismagilov et al. |

OTHER PUBLICATIONS

Invitation to Pay Additional Fees of the International Searching Authority, dated Jan. 4, 2019, from International Application No. PCT/US2018/055600, filed on Oct. 12, 2018. 14 pages.

International Preliminary Report on Patentability, dated Apr. 23, 2020, from International Application No. PCT/US2018/055600, filed on Oct. 12, 2018. 14 pages.

* cited by examiner

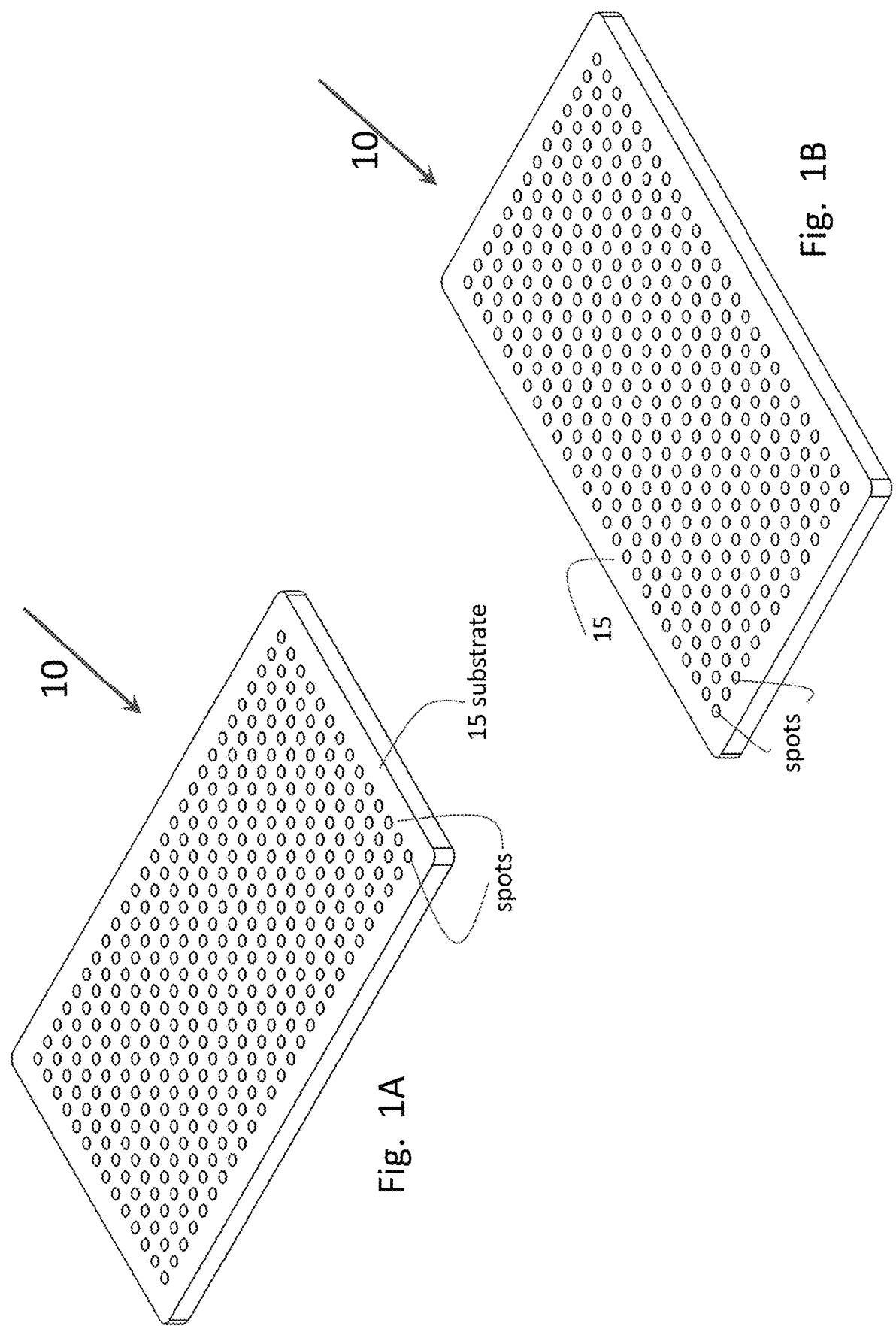

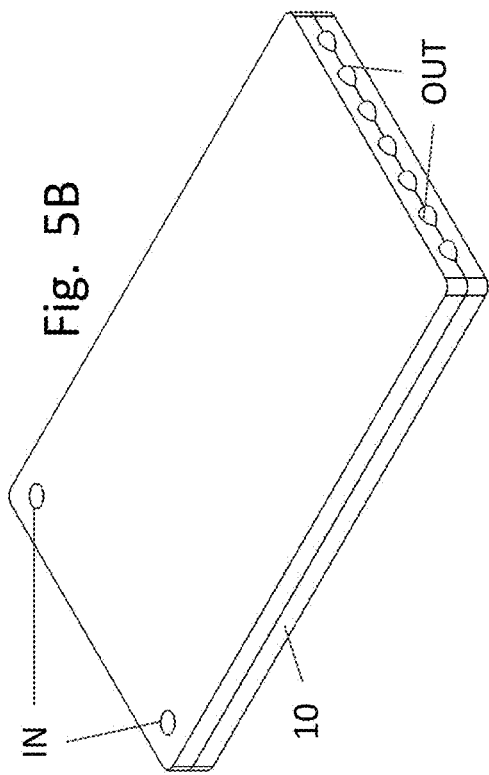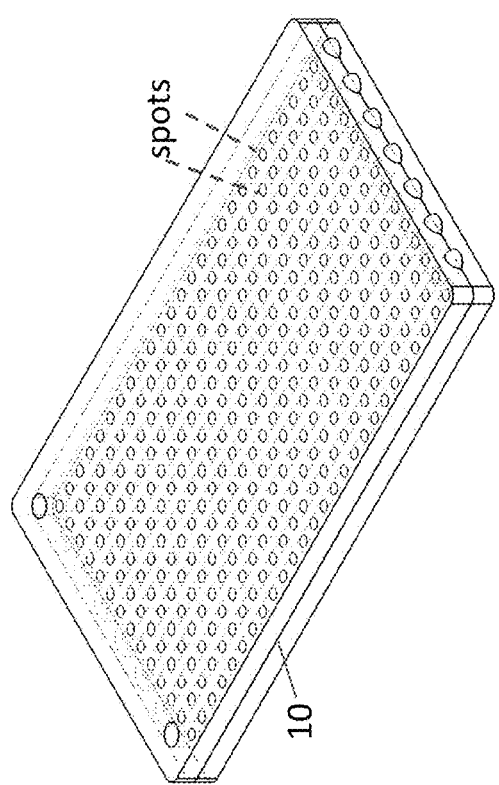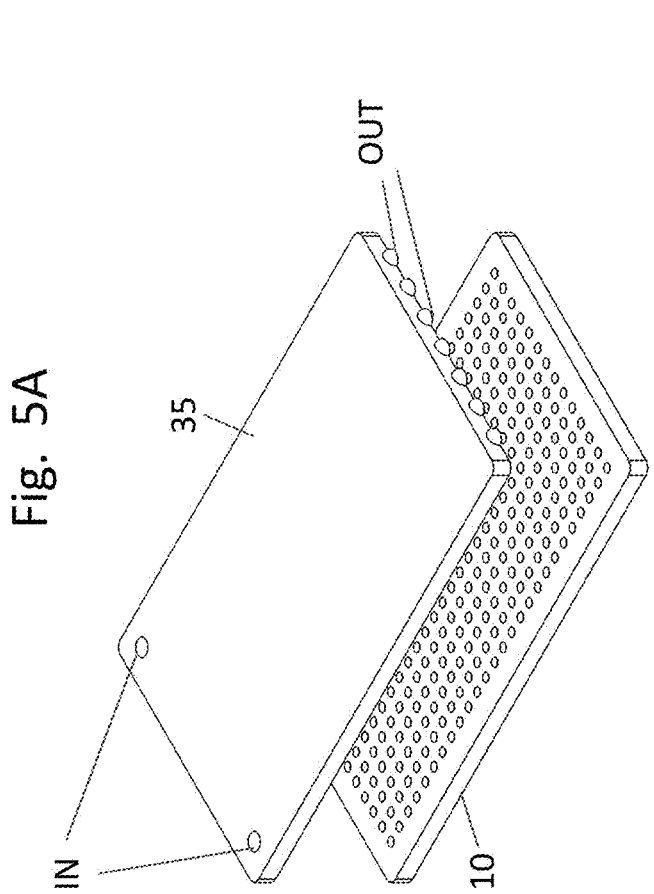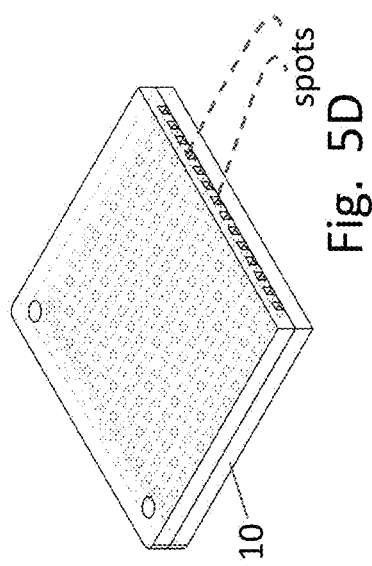

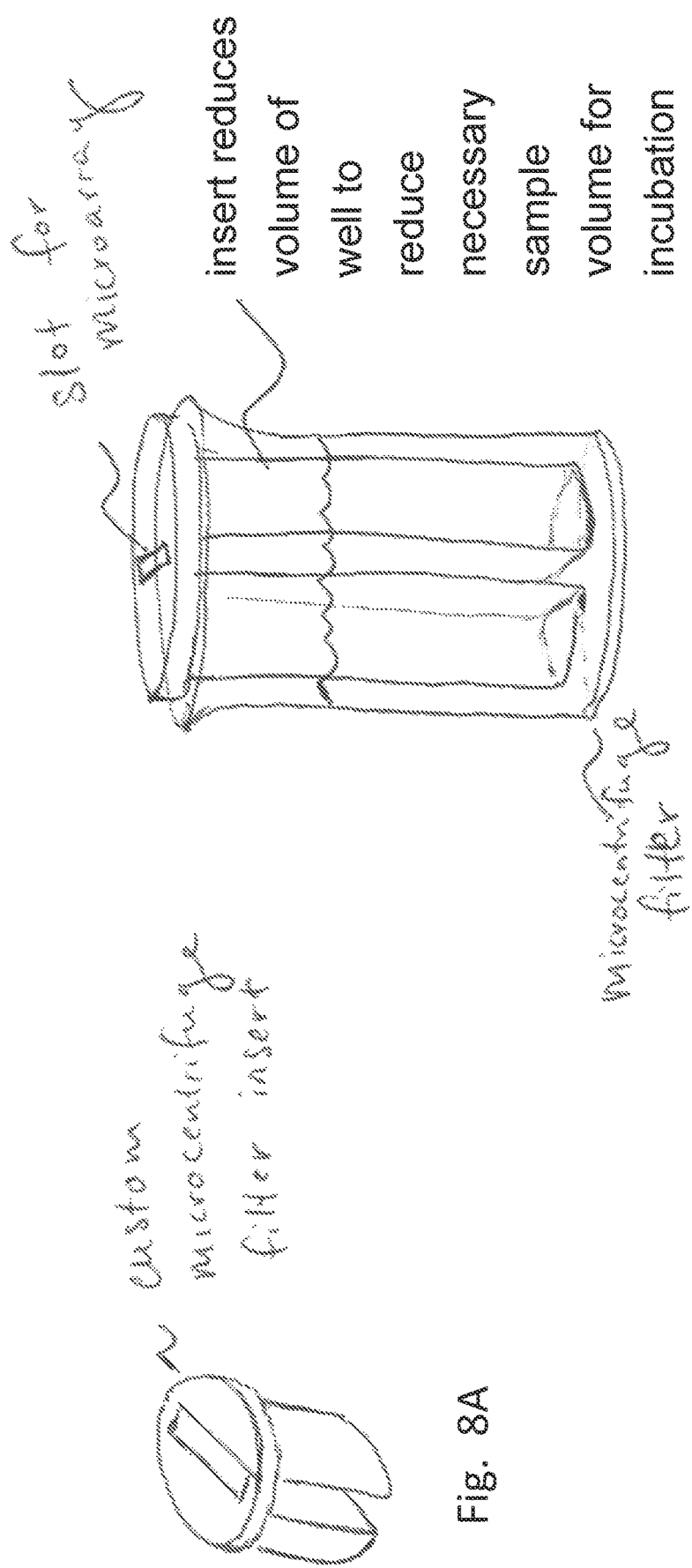

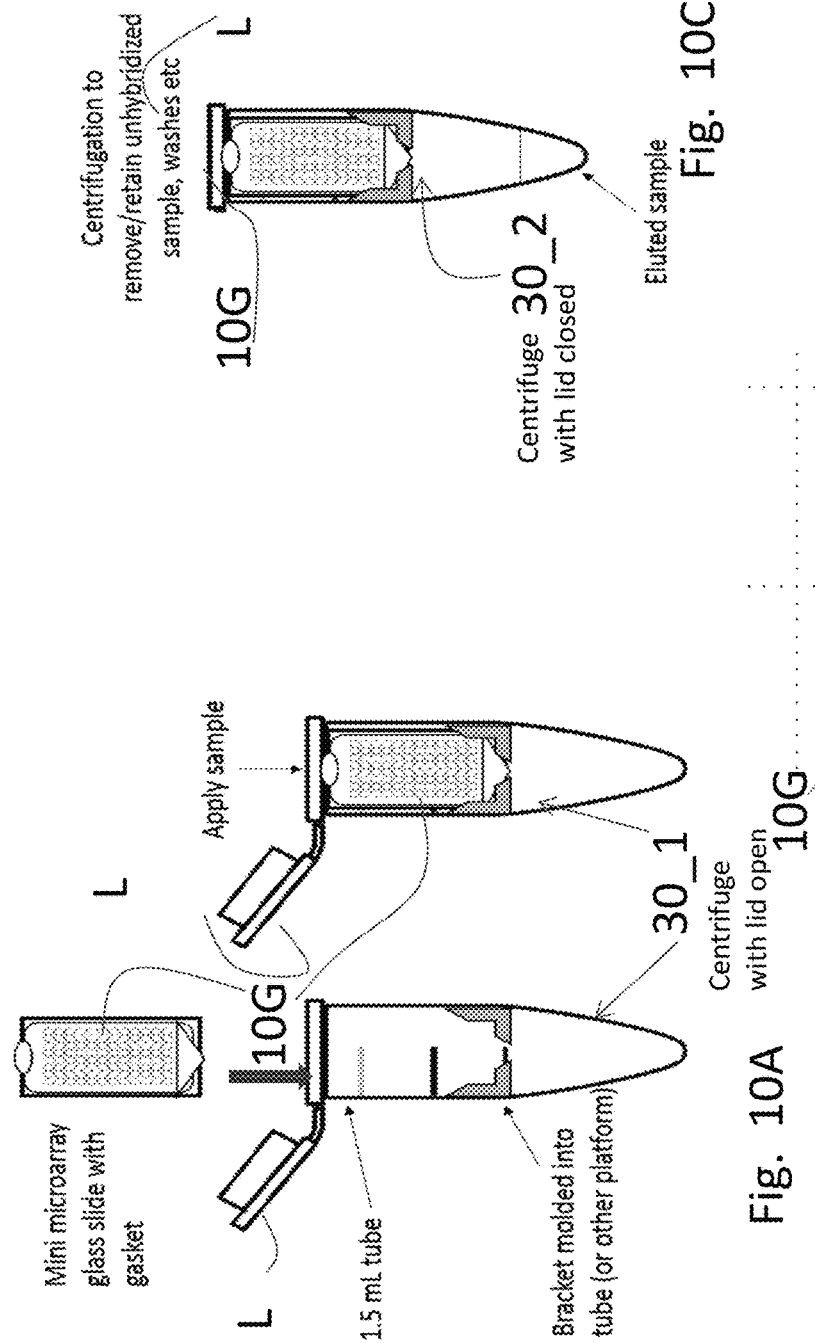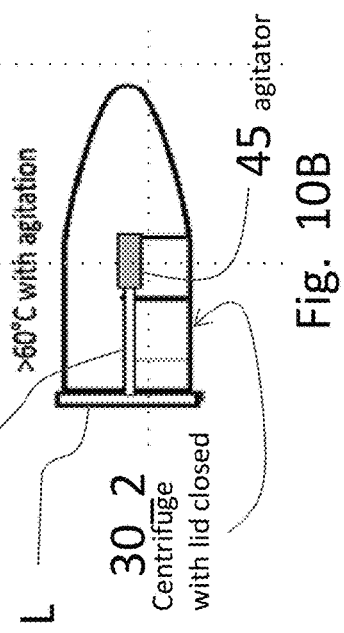

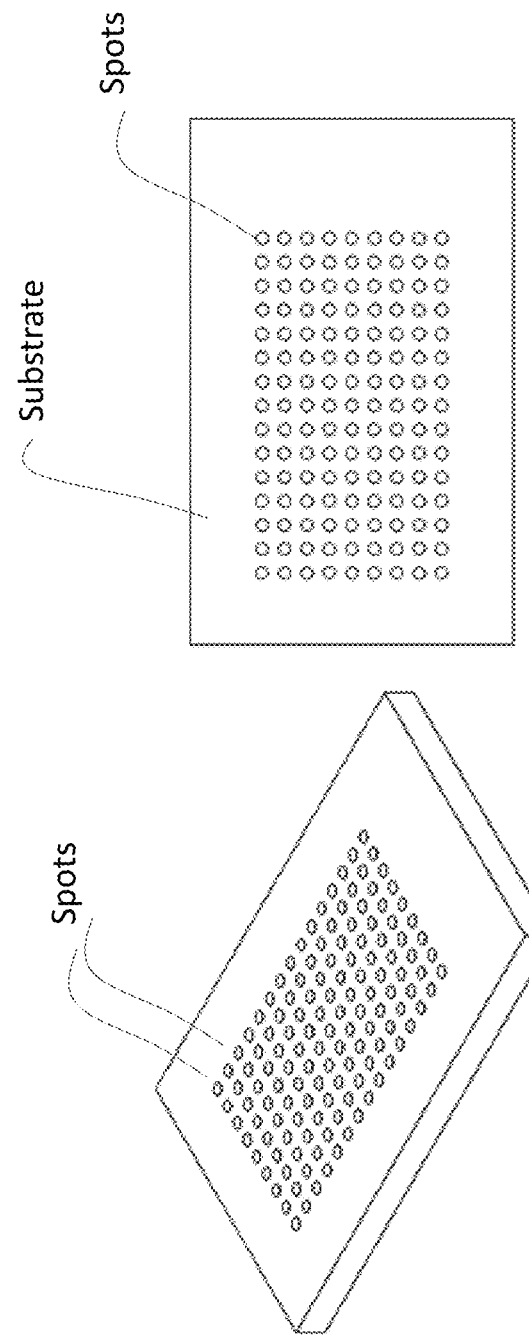

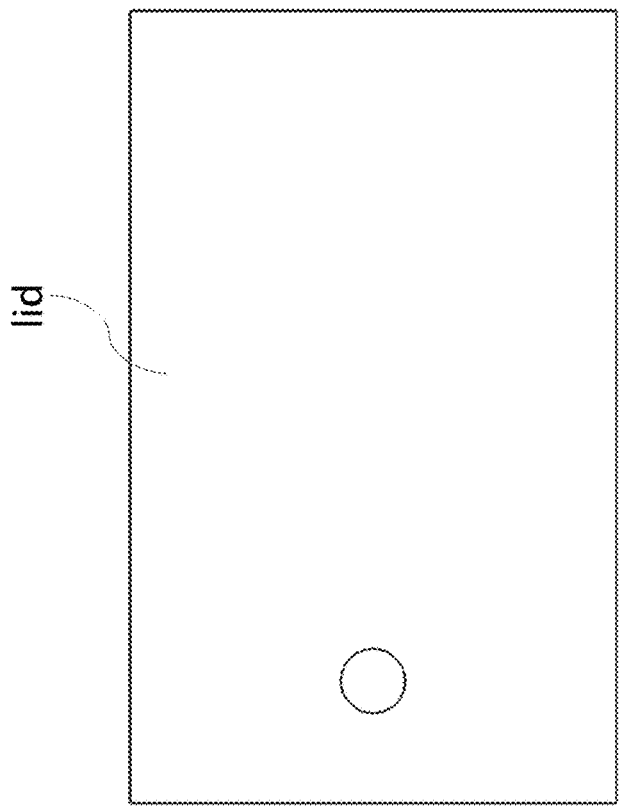
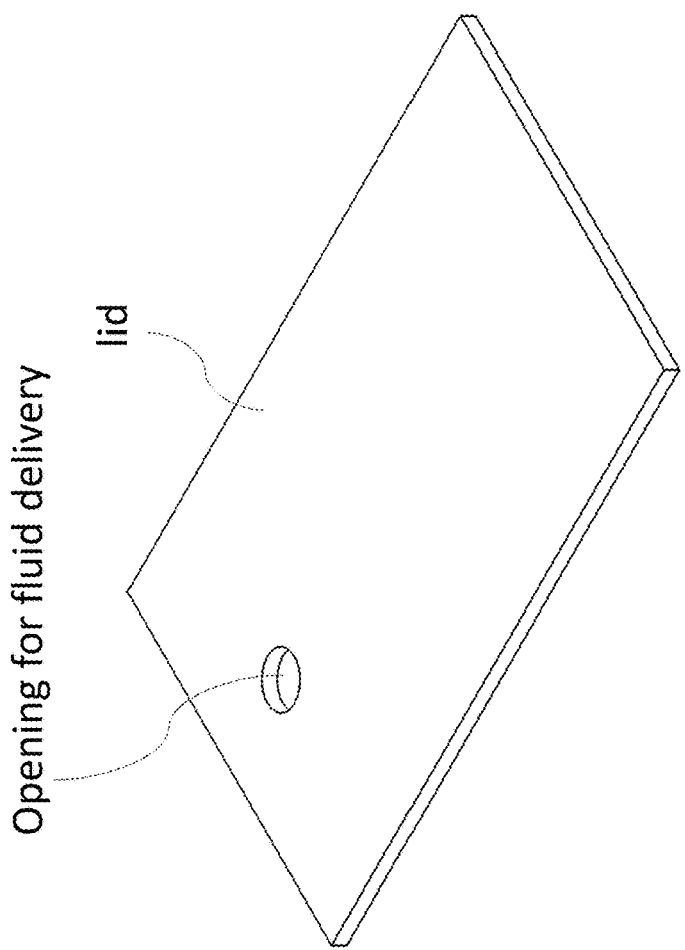
Fig. 14B
Fig. 14A

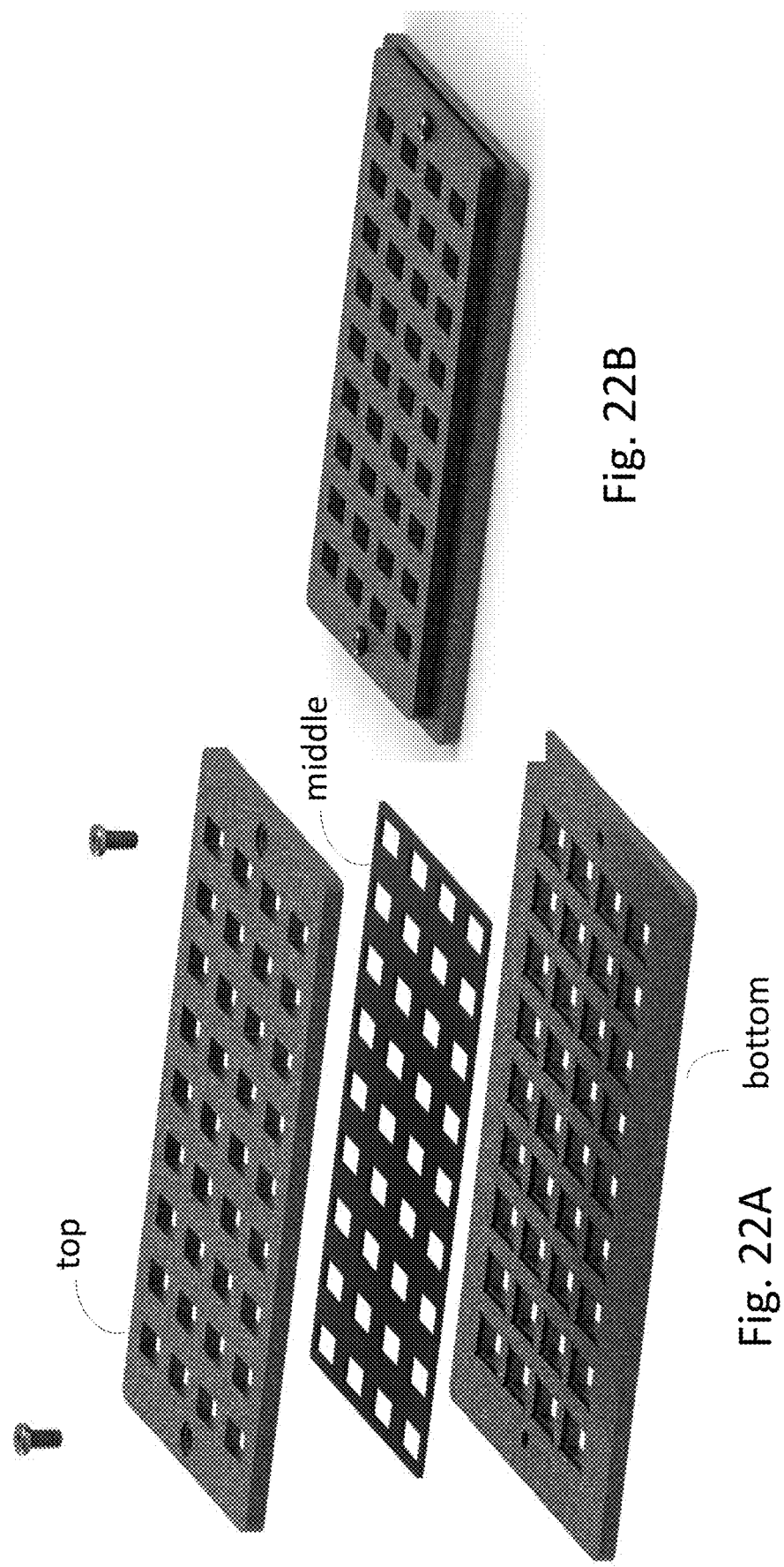

MINIATURIZED DNA MICROARRAY FOR SMALL-VOLUME SAMPLE PROCESSING

RELATED APPLICATIONS

This application is a 371 National Phase Application of international Application No. PCT/US2018/055600 filed on Oct. 12, 2018, now International Publication No. WO 2019/075321, published on Apr. 18, 2019, which International Application claims the benefit under 35 U.S.C. § 119(e) of U.S. Provisional Application No. 62/687,012, filed on Jun. 19, 2018, and U.S. Provisional Application No. 62/572,264, filed on Oct. 13, 2017, all of which are incorporated herein by reference in their entirety.

GOVERNMENT SUPPORT

This invention was made with Government support under contract number N6600118C4503, awarded by the IARPA. The Government has certain rights in the invention.

BACKGROUND OF THE INVENTION

DNA microarrays are comprised of collections of oligonucleotides, e.g., DNA, probes, which are spotted or printed in an array onto a solid support or substrate such as a glass slide. The standard size of the solid support is about the same size as a microscope slide. When these probes are exposed to a complementary target DNA in a sample, the probe and target DNA will hybridize and this hybridization reaction is generally detected optically.

Some limitations of conventional DNA microarray assays include the following: (1) the geometry and probe layout of the array lead to lengthy incubation times; (2) large target sample volumes are required: (3) no effort is made to conserve or to recover the sample; and (4) optical readout is a separate step which typically requires a specialized scanner.

SUMMARY OF THE INVENTION

As described herein, the present invention encompasses assemblies/apparatuses (also referred to herein as devices) comprising miniaturized DNA microarrays to allow for the processing and subsequent collection of very small sample volumes and to address some of the limitations of conventional DNA microarrays. Methods of their use are also encompassed by the present invention. Notable features include miniaturization of the supporting microfluidics, miniaturization of the array, and integration of the microfluidics array with the optical readout.

One embodiment of the present invention encompasses a miniaturized DNA microarray assembly, referred to herein as a "mini-microarray". More specifically, the miniaturized DNA microarray assembly comprises a high-density array of oligonucleotide probes printed on a solid substrate (typically an optically transparent surface); an inert gasket (i.e., the gasket material will not react with the sample or reagents, and should be heat tolerant at the selected incubation temperatures) surrounding the sides of the solid substrate, wherein the gasket has at least one fluid inlet port and at least one fluid outlet/exit port which allows fluid to enter the assembly, flow over and contact the oligonucleotide probes of the array in a time and temperature controlled manner under conditions suitable for a specific hybridization reaction between the sample containing one, or more oligonucleotides (e.g., DNA or RNA sequences) of interest. In some instances, the fluid will be pumped into the assembly, and in other instances capillary action can draw the fluid into the assembly. Sealed to the gasket/microarray solid support is an optically transparent top surface that allows for optical detection and determination of whether a hybridization reaction has occurred. The transparent top surface of the microarray assembly can comprise a serpentine channel in contact with, or contiguous with the inlet and outlet ports of the gasket, thus allowing controlled flow of fluid over the oligonucleotide probes of the array. Importantly, the size of the solid substrate of the array is significantly smaller than a standard DNA array slide and can be, for example, about 14.0 mm by about 8.0 mm, or more specifically about 11.0 mm by about 7.0 mm, or even more specifically about 11.0 mm by about 6.75 mm.

The array of oligonucleotide probes printed on the substrate is typically a high-density (also referred to herein as "ultra-high" density) DNA microarray. Printing can be accomplished using precision fluid dispensers, and printing can be on both sides of the substrate. Spots of DNA can be as small as about 20 μm in diameter with a pitch as small as about 50 μm. This density will provide a full array of about 30,000 to about 50,000 individual spots to be printed on a substrate. At this density, an array of about 30,000 individual spots can be printed on a substrate of dimensions of about 11.0 mm by about 6.75 mm. A substrate of about 11.0 mm by about 6.75 mm is small enough to be inserted into a standard microcentrifuge tube (e.g., 1.5 ml). Fluid volume to completely fill/cover the full microarray sitting vertically in a microcentrifuge tube would be about 950 μl. Alternatively the array can be a partial array containing fewer probes. For example, if the mini microarray would sit vertically in a transwell filter apparatus or the microcentrifuge tube, the number of spots can be about 3600/mm×height of the fluid column (mm) in the filter/tube. Volume would be about 63 μl/mm×height of fluid column (mm) and about 57 probes/μl of sample. Another example would be if the mini microarray would sit horizontally in the transwell filter apparatus or microcentrifuge tube. The number of probes on the array would be about 30,000 to about 45,000 to about 50,000 and the sample volume required to cover the array in this position would be about 100 μl, or about 500 probes/μl of sample. For example, the substrate size would be about 6.75× about 11 mm.

Alternatively, the miniaturized DNA microarray assembly comprising a high-density array of oligonucleotide probes printed on a solid substrate can be enclosed within an inert container/chamber (also referred to herein as an enclosure) surrounding the sides and bottom of the mini-microarray on the solid substrate. The enclosure has a fluid inlet port and a fluid outlet/exit port which allows fluid to enter the container, flow over the mini-microarray and contact the oligonucleotide probes of the array. Typically the enclosure also has an optically transparent top surface sealed to the enclosure which allows for an optical detection means to detect a hybridization reaction. The enclosure can be open on one end to allow a mini-microarray substrate to slide in and out of the enclosure.

One side of the enclosure can also comprise a rupturable or removable barrier over the entire edge of the side. The barrier can also comprise small plugs at the end of channels formed within the enclosure and running above the mini-microarray. The breakaway barrier allows for fluid flow over the mini-microarray but then further allows recovery of sample after breaking or removing the barrier (e.g., by centrifugation). For example, the barrier could be a membrane that ruptures due to g-force. Alternatively, it could be a small hole that has enough surface tension that liquid will not come out until centrifugation.

In another embodiment of the present invention, a miniaturized DNA microarray assembly comprising a high-density array of oligonucleotide probes printed on a solid substrate is placed into a microcentrifuge tube that has been modified/adapted to support/securely hold the array in a stable manner during centrifugation. The support/holder formed in the interior of the microcentrifuge tube can comprise a bracket affixed to, molded into, or formed on, the inside walls of the tube to securely support the mini-microarray during the hybridization and washing steps and subsequent centrifugation. Sample can be eluted off the mini-microarray supported in the microcentrifuge tube and, after centrifugation, is collected at the bottom of the tube for recovery.

Alternatively, a microcentrifuge tube filter apparatus/device or insert (e.g., a transwell) can provide the support for the mini-microarray. Such devices are designed to fit inside of a microcentrifuge tube. For example, sample can be eluted off the mini-microarray and the unhybridized DNA is collected on the top of the filter surface.

Also encompassed by the present invention are methods of assaying a sample for one, or more, oligonucleotide sequences of interest (also referred to herein as the target DNA). The sample can be any biological sample suitably processed for assay with the mini-microarray assemblies, apparatuses or microfluidic devices described herein. More specifically, the sample can be e.g., whole blood, serum, plasma, urine, cerebral spinal fluid, wound exudates or tissue homogenate. As described herein, the sample volume required for assay with the mini-microarray of the present invention is significantly smaller than required for other standard DNA array assays.

Suitable conditions (e.g., incubation time and temperature) and reagents (e.g., incubation buffer and wash buffers) for a specific hybridization reaction between the sample oligonucleotide and arrayed oligonucleotide probes are well known to those of skill in the art. As described herein, because of the small sample size required for the mini-microarrays of the present invention, reactions time can be accelerated. Moreover, the mini-microarray assemblies, apparatuses and devices as described herein are designed for optical detection of a hybridization reaction (e.g., using fluorescent tags) and can be adapted for read-out by standard optical means.

The advantages of the present invention are many. The present approach includes the construction of a mini-microarray to enable low-volume analysis and conservation of high value samples. There are numerous technical benefits to mini-arrays over traditional microarrays. Traditional microarrays represent higher risk of sample loss through evaporation due to the relatively large surface area and temperatures applied to allow for the hybridization reaction to take place. As described herein, the mini-microarray can be enclosed or encapsulated in a chamber/container to minimize sample volume and loss. In some embodiments, the mini-microarray will encapsulate the target sample in a sealed chamber that will fit into a microcentrifuge tube, (e.g., a 1.5-2 milliliter (ml) tube) allowing for centrifugation and recovery of unhybridized sample, which can be analyzed downstream. High-stringency washes that allow for high specificity of hybridization can be also be recovered. Additionally, a dehybridization reaction can also be carried out in the chamber, allowing further analysis of the specific hybridization events after scanning of the mini-array spots.

The present approach enables the combination of the aspects of the mini-microarray with microfluidic and optical hardware. The present microfluidic device can be comprised of a fluid channel that will sit atop a high-density microarray. The microarray probes can be spotted on a transparent surface (i.e., a glass slide) that will form the bottom wall of the channel. Closed-loop pressure-driven flow will enable the sample to be passed over the array (e.g., in a cyclic or serpentine manner as dependent on the channel formation) to maximize interaction between sample oligonucleotides/DNA of interest and nucleic acid probes. This will reduce incubation time and will increase overall binding efficiency.

In addition, the high specificity of traditional microarray assays will be maintained by the increased interaction between target sample and microarray probes. Completely enclosing the liquids will enable handling of small aqueous sample volumes (e.g., about or less than 10 µL). Following the incubation period, any un-hybridized sample can be extracted from the device for further downstream processing.

The hardware components will provide a multiplexed, optical readout with high sensitivity and specificity, enabling interrogation of samples and permitting recovery of both hybridized and non-hybridized samples to allow downstream testing in further assays.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. Some but not all drawings are to scale; emphasis has instead been placed upon illustrating the principles of the invention. The patent or application file contains at least one drawing executed in color. Copies of this patent or patent application publication with color drawings(s) will be provided by the Office upon request and payment of the necessary fee. Of the drawings:

FIGS. 1A and 1B show two isometric views (perspective views, looking down) of a DNA microarray to scale according to the present invention.

FIG. 2B is a transparent (optically clear) version of the chamber shown in FIG. 2A.

FIG. 3A shows the chamber being lowered for position on the microarray. FIG. 3B shows the microarray with the chamber positioned snuggly on top. FIG. 3C is a transparent chamber version of the FIG. 3B. FIG. 3D shows a cross-section of the assembly of FIG. 3B, cut parallel to the width of the assembly.

FIG. 4B is a transparent version of FIG. 4A. The embodiments have inlets for inflow of sample and outlets for outflow of excess sample and other liquid. Some versions encompass outlets at the end of each serpentine channel.

FIGS. 5A, 5B, 5C and 5D show isometric and cross-sectional views of the serpentine chamber fitted on top of the microarray. FIG. 5A shows the chamber being lowered for position on the microarray. FIG. 5B shows the microarray with the chamber positioned snuggly on top. FIG. 5C is a transparent chamber version of the FIG. 5B. FIG. 5D shows a cross-section of the assembly of FIG. 5B, cut parallel to the width of the assembly.

FIGS. 8A and 8B are perspective views of a custom microcentrifuge filter insert inside a microcentrifuge filter apparatus for use in the embodiment of FIG. 4. A gasket (or space-filler) can be added to the microcentrifuge spin column to hold the microarray firmly in place and to reduce the internal volume of the column, allowing the entire incubation process to take place inside a microcentrifuge tube.

FIGS. 10A, 10B and 10C show exemplary steps of a mini-microarray assay in a microcentrifuge tube. The mini microarray is enclosed in a gasket and can be inserted in a vertical or horizontal position. The entire apparatus (DNA microarray with custom hybridization chamber) is prepared, filled with sample, left in a microcentrifuge tube for the duration of the hybridization process and then placed in a microcentrifuge tube to elute and collect the unused sample.

FIGS. 11A and 11B show a DNA microarray (multiple views) with epoxysilane on a glass substrate 11.0 mm×6.75 mm×0.7 mm.

FIGS. 14A and 14B show a lid (multiple views) of polycarbonate 11.0 mm×6.75 mm×0.25 mm with an about 0.9 mm hole/opening for delivery of fluid.

FIGS. 22 A and B depict a chiplet fixture for imaging of the assembled microarrays having the same footprint as a 96-well microtiter plate.

DETAILED DESCRIPTION OF THE PREFERRED EMBODIMENTS

Figure 2B:
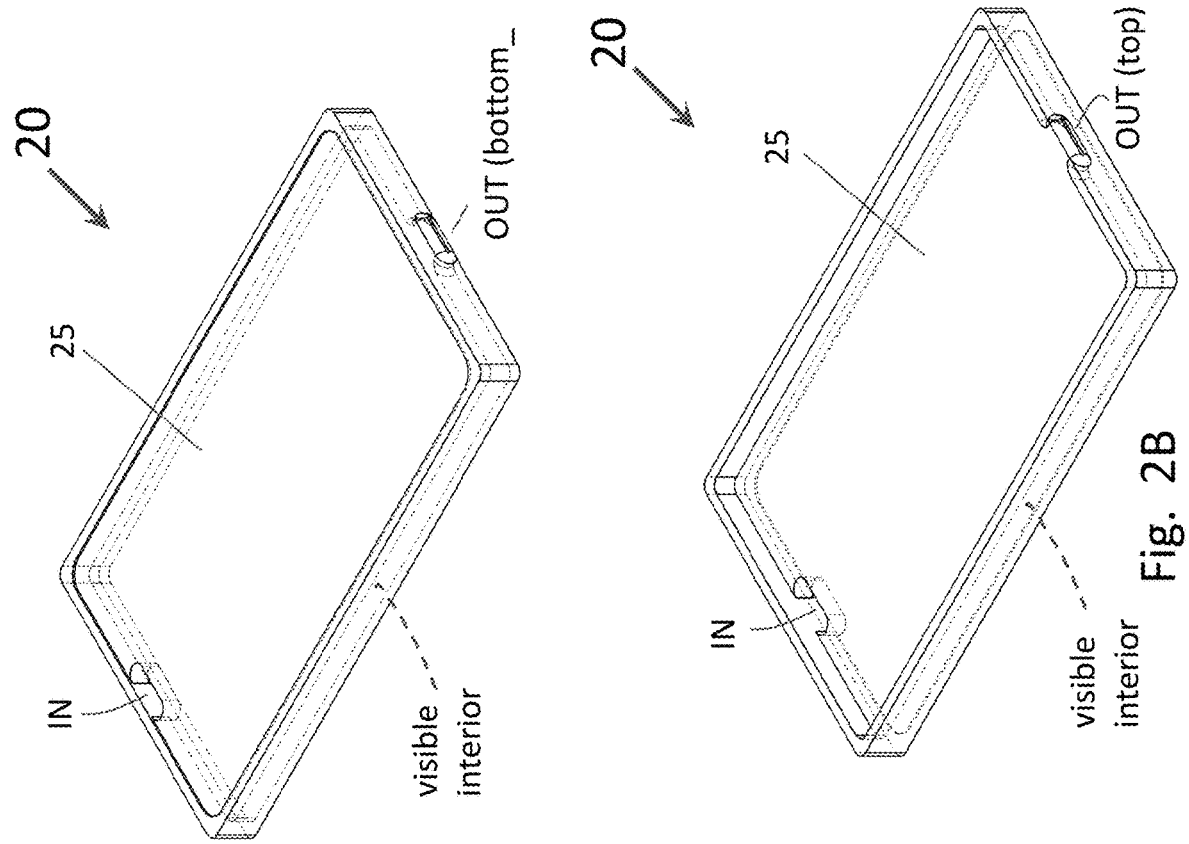
FIGS. 2A and 2B are isometric views of the chamber for enclosing the top of the microarray. The embodiments show inflow and outflow openings for sample.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Embodiments of the present invention utilize an ultra-high-density DNA microarray of probe spots which is meant to interface with a small sample volume and to allow optical access to the array during the incubation period. As used herein, the term "sample" can encompass "sample of target species", as well as "oligonucleotide of interest" or simply "target". Note that from hereinafter, the term "microarray" and "array" will denote "mini-microarray". A sample can be any fluid comprising the target of interest, such as a bodily fluid such as blood, plasma, serum, cerebral spinal fluid, urine obtained from a subject.

The array may be printed on one of a variety of materials, substrates providing solid support, which may be optically transparent or opaque, including glass, PMMA (poly-methylmethacrylate), COP (cyclo-olefin polymer) or COC (cyclic-olefin copolymer), among others. The materials may have a surface coating such as epoxysilane, to assist in stable probe spot formation and in probe binding. Other suitable surface coatings compatible with the substrate and with properties suitable for stabilizing spot formation are known to those of skill in the art and can include, for example streptavidin, polylysine and other suitable reagents. Optionally, a reflective layer such as a gold or sulfur reflective layer, can be included under the surface coating. The array comprises discretely spaced spots of specific oligonucleotide probes (either all of the same oligonucleotide or of different oligonucleotides). Individual spots on the array may be as small as 5 micrometers (μm) or as large as 1 millimeter (mm) in diameter with a center-to-center pitch as small as 10 μm or as large as 2 mm. The array may completely cover the surface of the substrate or may only cover a partial section of the available area. FIGS. 1A and 1B show two isometric views (perspective views, looking down) of a DNA mini-microarray 10 to scale according to the present invention. FIG. 1A is a schematic of the array, substrate 11 size of about 11.0 mm× about 6.75 mm. However, the dimensions can be larger or smaller. FIG. 1B shows an alternate orientation of the microarray 10.

In some embodiments both sides of the array substrate may be used to increase probe density, however, the substrate must then be opaque for detecting the hybridization reactions on both sides of the arrayed substrate.

Figure 2A:
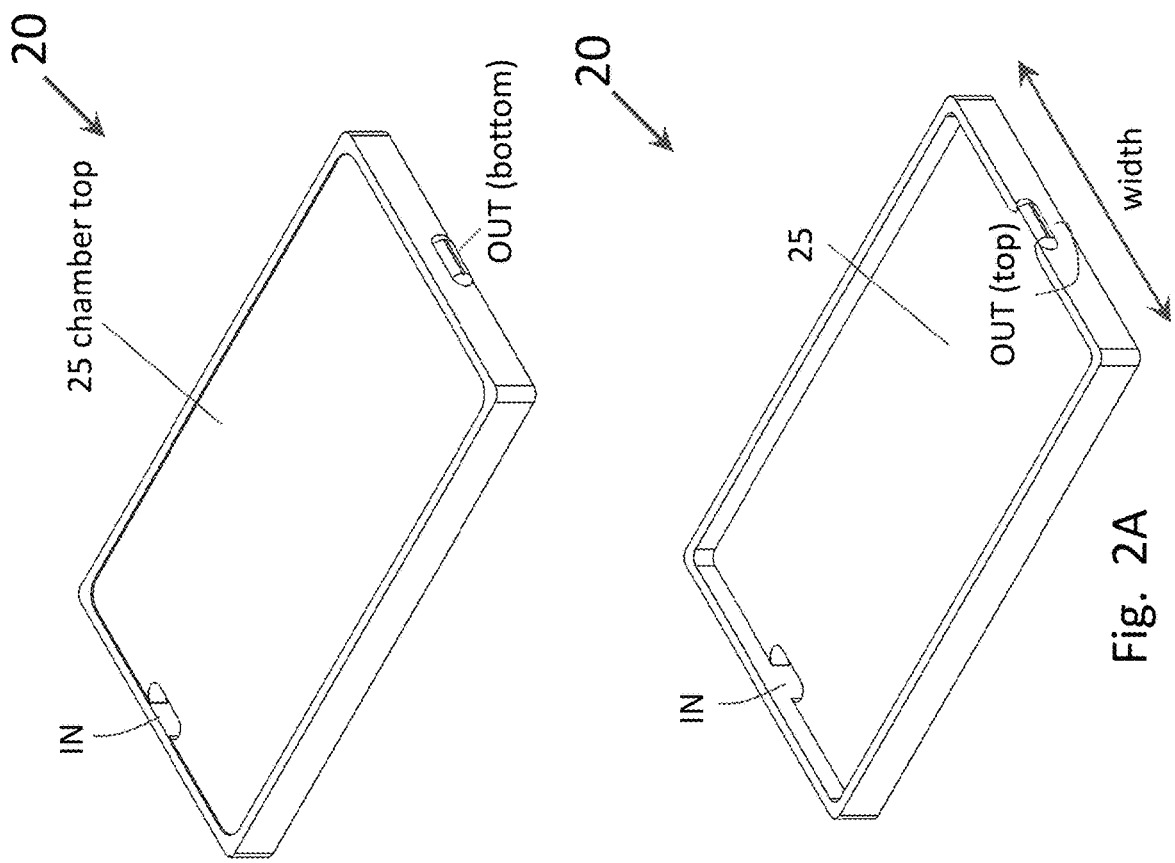

FIGS. 2A and 2B show various embodiments (to scale) of a rectangular chamber 20 to fit snuggly on top of the microarray 10. In all embodiments the inflow opening/hole (IN) is for inserting sample for hybridization and is on top. The outflow opening/hole (OUT) for expelling unused sample and other liquids can be either on top and bottom. Both IN and OUT are along the smaller dimension, width, of the enclosing chamber. FIG. 2B shows that the chamber may be transparent (glass or plastic) for monitoring progress of hybridization. In FIG. 2B one can see the interior through the chamber 20 as the chamber top 25 may be optically transparent. The other sides (not just the top 25) of the chamber can also be transparent.

FIGS. 3A through 3D show the chamber 20 (with top 25) laid on top of the DNA microarray 10. The views are isometric and to scale. All embodiments show the outflow (OUT) in the bottom of the chamber, but the outflow can alternatively be on top.

Figure 3B:
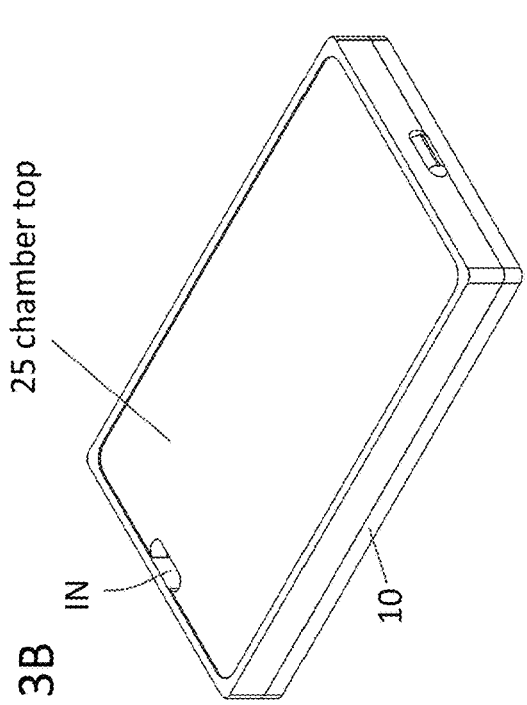
FIGS. 3A, 3B, 3C and 3D show isometric and cross-sectional views of the chamber fitted on top of the microarray.
Figure 3C:
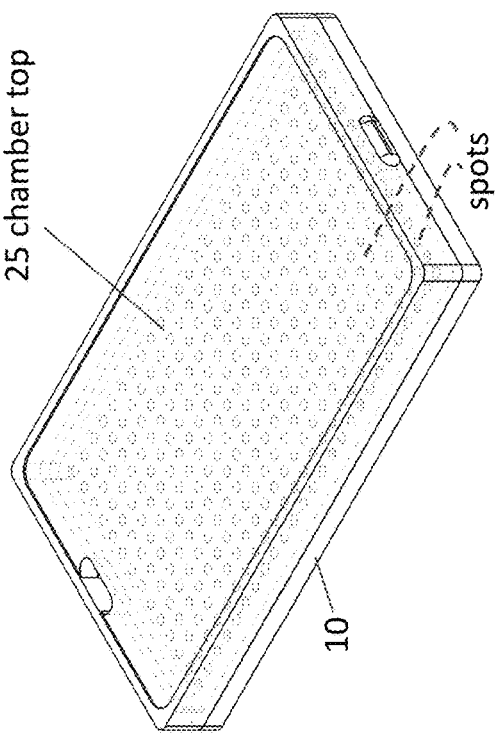
Figure 3A:
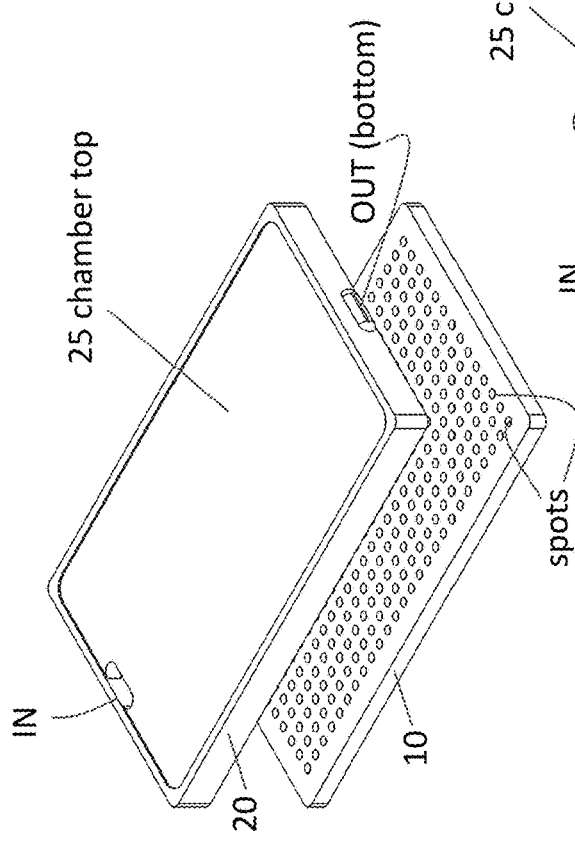

FIG. 3A shows the chamber 20 being prepared to go on top of the DNA microarray 10. Although not shown a rectangular gasket may be inserted between the chamber 20 and the microarray 10 for leak proof fitting of the array and the chamber.

FIG. 3B shows the chamber 20 fitted over the microarray 10. FIG. 3C is a transparent version of the chamber 20 laid on top of the microarray. The advantage of a transparent chamber is that it allows for optical monitoring of the progress of hybridization. FIG. 3C shows the visible spots on the microarray through the transparent chamber top 25.

The sample will be loaded into the well (using fluid inlet IN) and will hybridize with probes on the DNA microarray surface. The small volume of the enclosure (about 1- to about 100 μl; preferably 1-10 μl, and for example, more specifically can be about 5.3 μl) will reduce the amount of target sample necessary, relative to state-of-the-art techniques, to achieve probe-target binding. The sample may sit unperturbed during the incubation period or closed-loop pressure-driven flow will enable the sample to be passed over the array in a cyclic fashion to maximize interaction between targets and nucleic acid probes. This will reduce incubation time and will increase overall binding efficiency. The high specificity of conventional DNA microarray assays will be maintained by the increased target-probe interaction. The closed nature of the system will prevent evaporative sample loss and will enable the recovery of unhybridized sample following the incubation period. In addition, the top/ceiling surface of the chamber, or, alternatively, the entire device surface, will be optically transparent to enable detection (read out) using standard optical techniques (i.e., fluorescence detection).

Figure 3D:
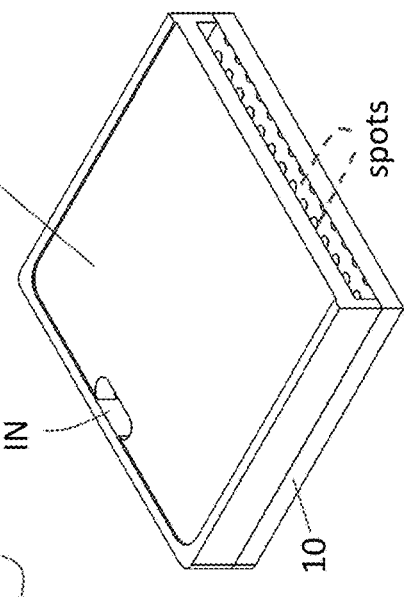

FIG. 3D shows an end view of the mini-microarray and the chamber.

Figure 4B:
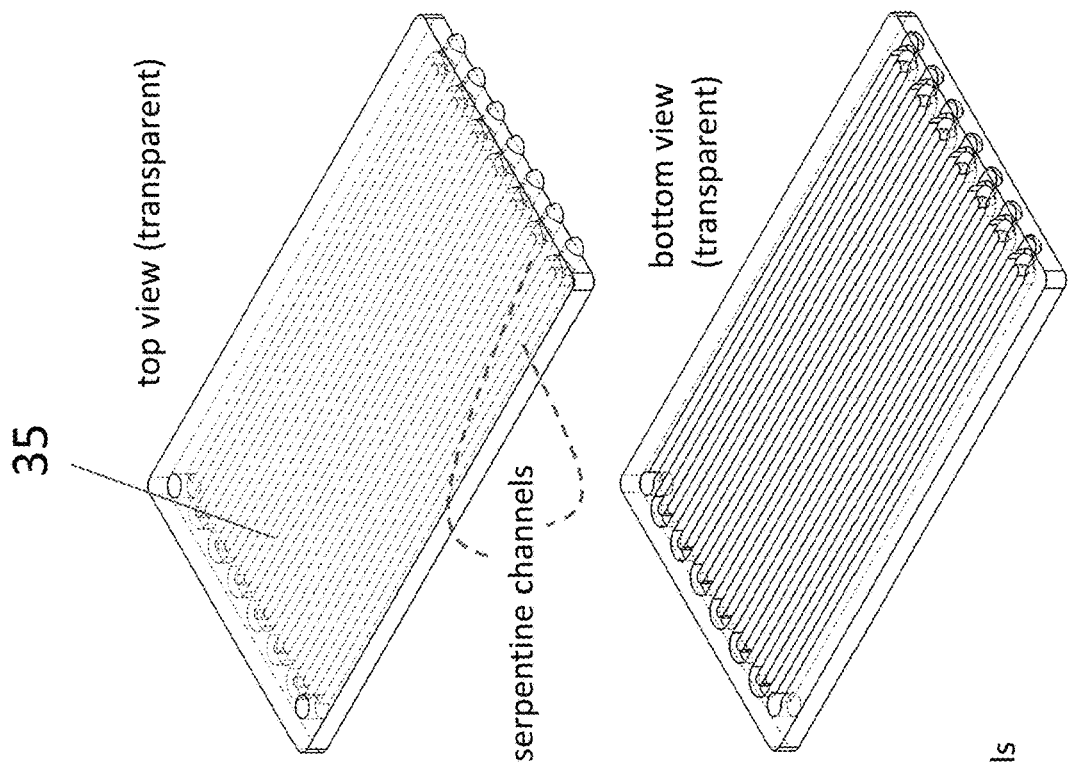
FIGS. 4A and 4B are isometric views showing (to scale) microfluidic channels constructed in the interior (bottom of cover) of the microfluidic chamber. Both figures show top and bottom views of the chamber top.
Figure 4A:
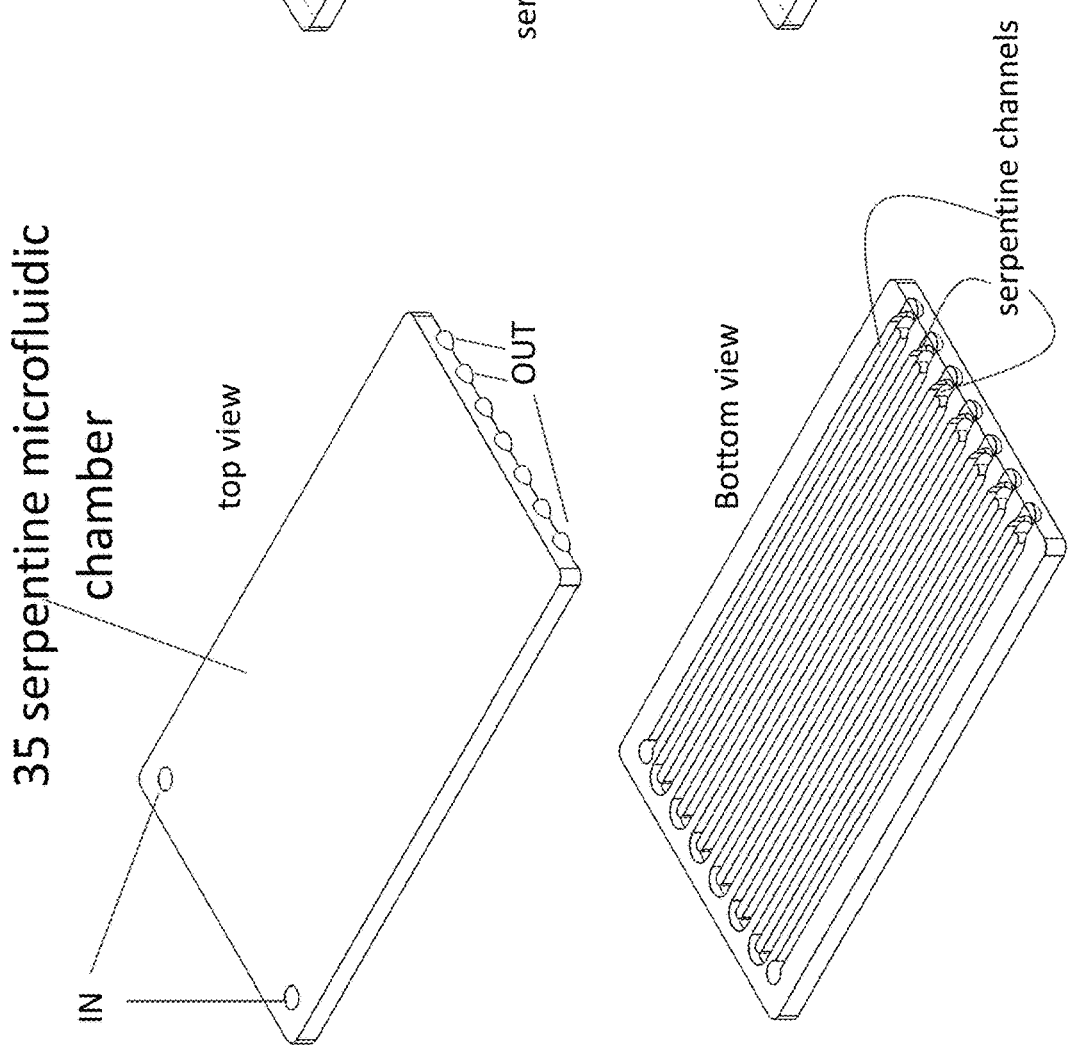
Figure 6D:
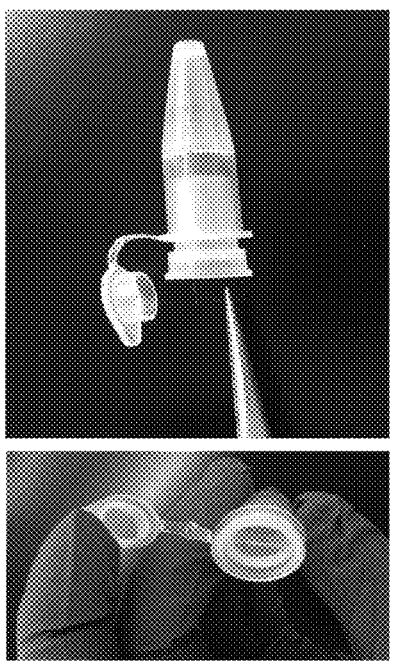
FIGS. 6 A-E is an embodiment of the mini microarray inserted in a microcentrifuge tube filter apparatus using the microarray of FIGS. 1A and B. Incubation is in a microcentrifuge spin column. The microarray can be completely enclosed (serpentine or large chamber) and a gasket can be added to the column to hold the microarray firmly in place.
Figure 6A:
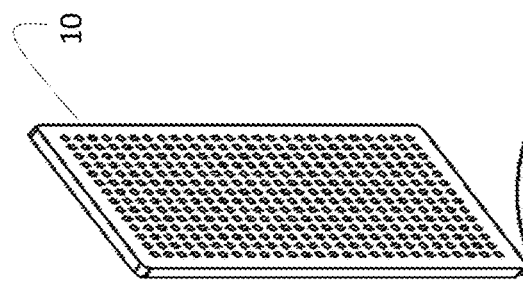
Figure 6E:
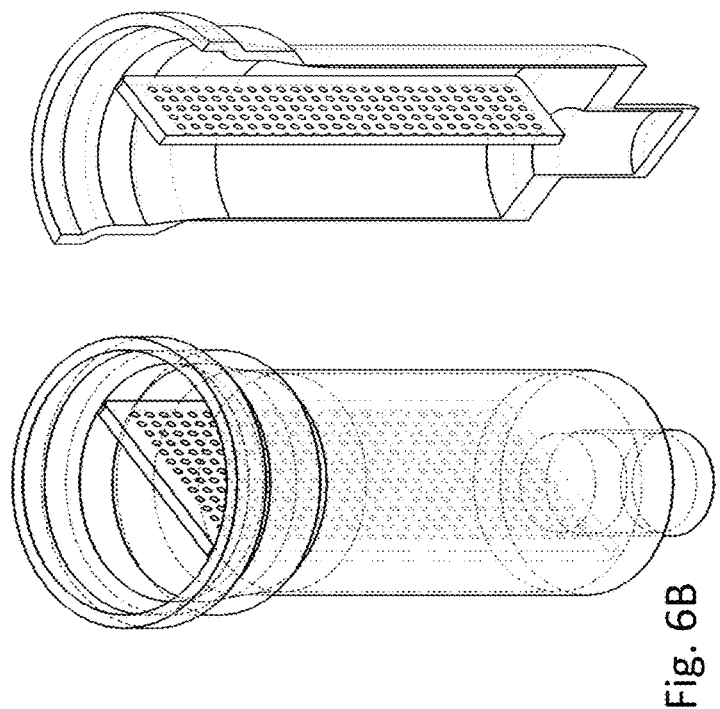
Figures 6B, 6C:
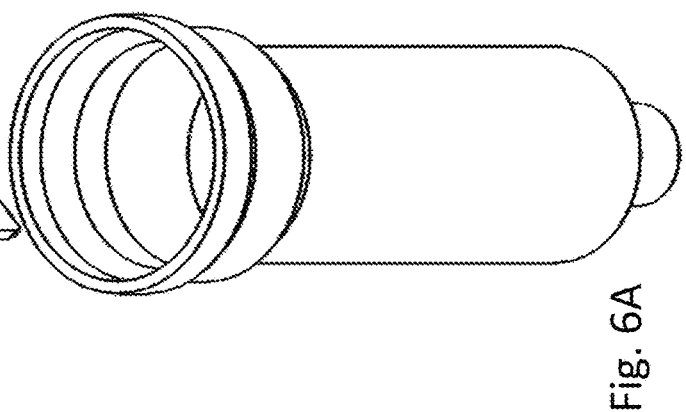

Alternatively, as shown in FIGS. 4A and 4B, serpentine microfluidic channels are constructed to sit directly atop the DNA microarray to allow for even further reduction in the fluid volume. FIG. 4A shows the top of the serpentine chamber 35 with IN showing inflow for sample. Each serpentine tube has an outflow OUT exit. The second figure in FIG. 4A shows the bottom of the serpentine chamber which shows the serpentine channels more clearly. FIG. 4B is a transparent version of the two views shown in FIG. 4A.

FIG. 5A shows the chamber 35 being prepared to go on top of the DNA microarray 10. Although not shown a rectangular gasket may be inserted between the chamber 35 and the microarray 10 for leak proof fitting of the array and the chamber.

FIG. 5B shows the chamber 35 fitted over the microarray 10. FIG. 5C is a transparent version of the chamber 35 laid on top of the microarray. The advantage of a transparent chamber is that it allows for optical monitoring of the progress of hybridization. FIG. 5C shows the visible spots on the microarray through the transparent chamber top 35. FIG. 5D shows an end view of the mini-microarray and the chamber.

The transparent DNA microarray forms the bottom surface of the channels. The sample will be loaded into the channels and exits out of the channels using a set of fluid ports placed in the roof of the enclosure. The channels will be arranged in a serpentine pattern and will be spaced such that the fluid path matches the center-to-center pitch of the microarray spots.

FIG. 6 A-E is an embodiment of incubation in microcentrifuge tube filter. The microarray may be completely enclosed (serpentine or large chamber) and a gasket may be added to the filter to hold the array firmly in place. (Microcentrifuge tube filter is shown only for illustrative purposes as the dimensions do not exactly match commercial filter as drawn.)

Figure 7:
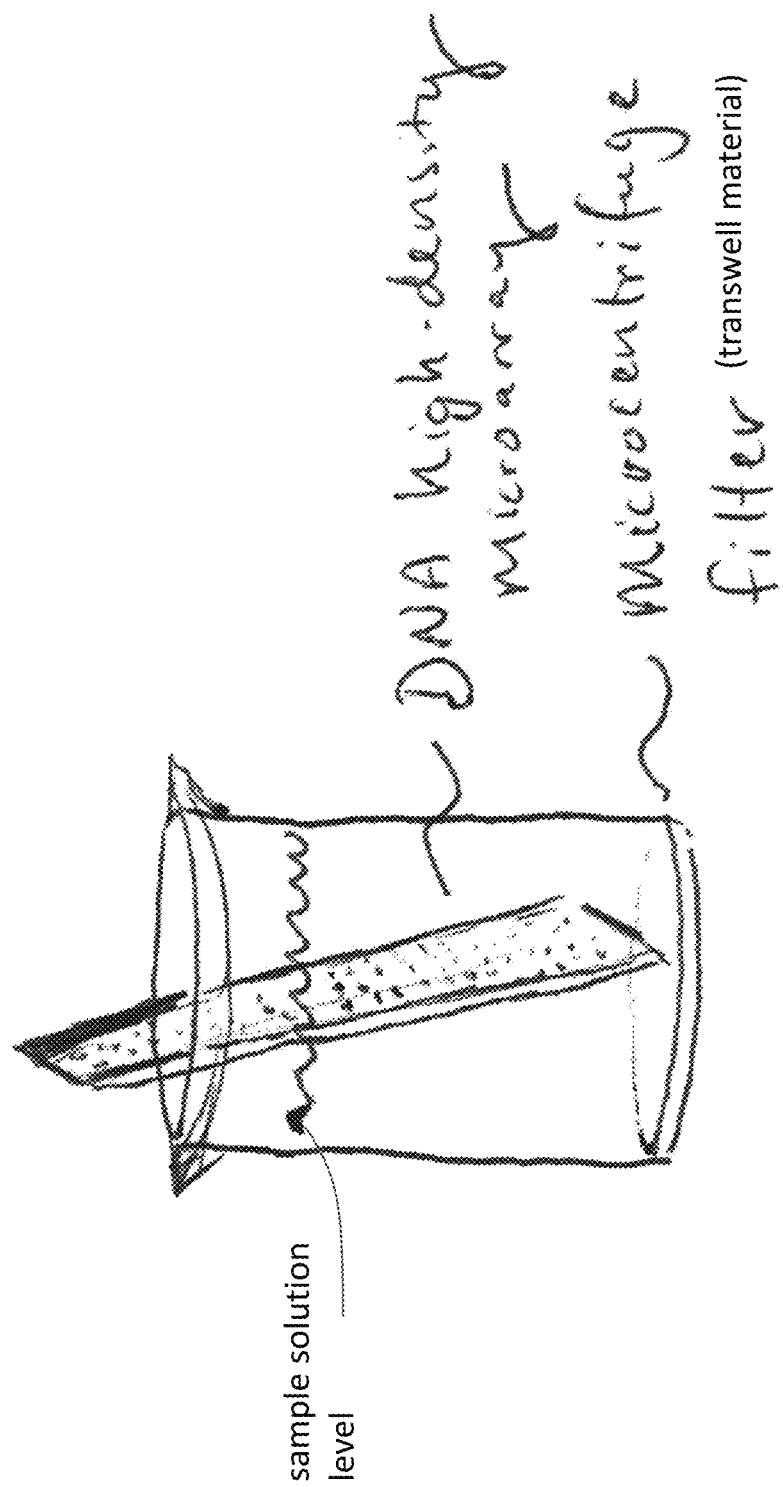
FIG. 7 is an embodiment of the DNA microarray positioned vertically inside a microcentrifuge filter apparatus for the incubation process.
Figure 9A:
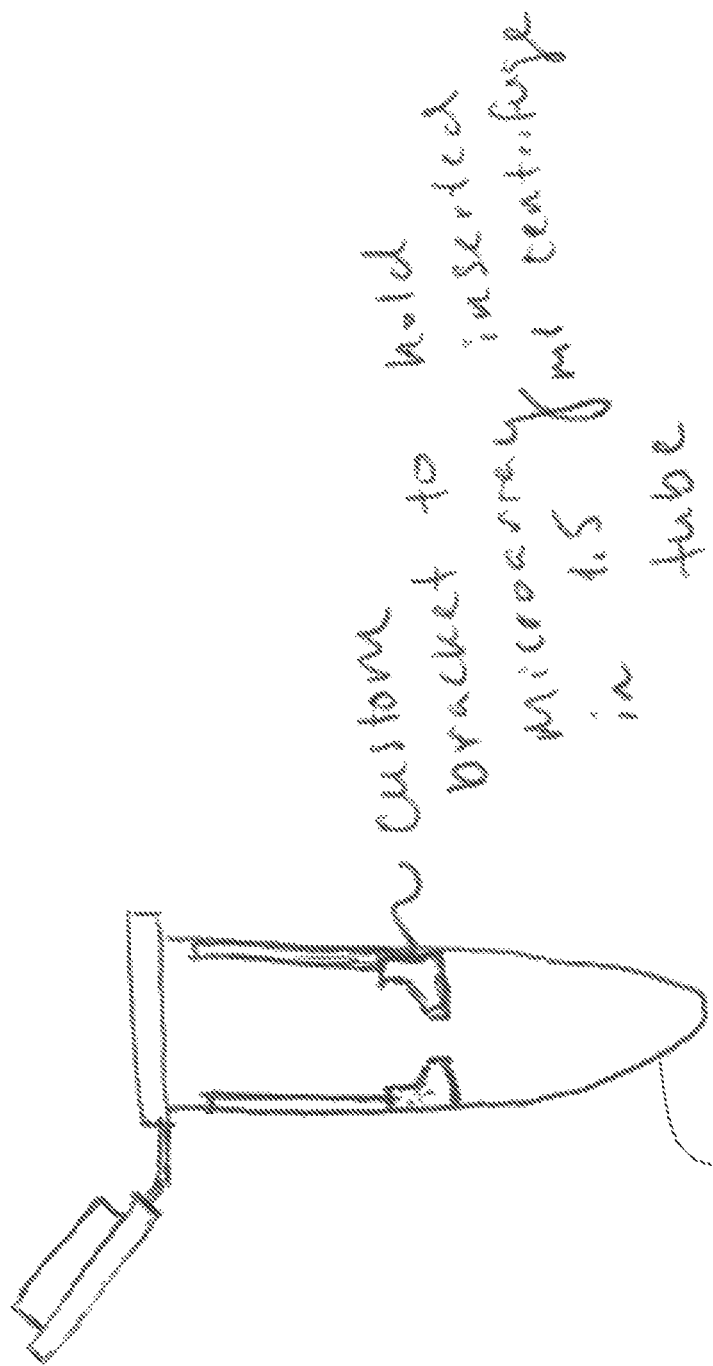
FIGS. 9 A-B show side views of an alternative gasket design that can be added to the 1.5 ml microcentrifuge spin column to hold the array firmly in place and to reduce the internal volume of the column. In this embodiment the microarray is inserted into the bracket and sample solution held in the upper half of the tube.
Figure 9B:
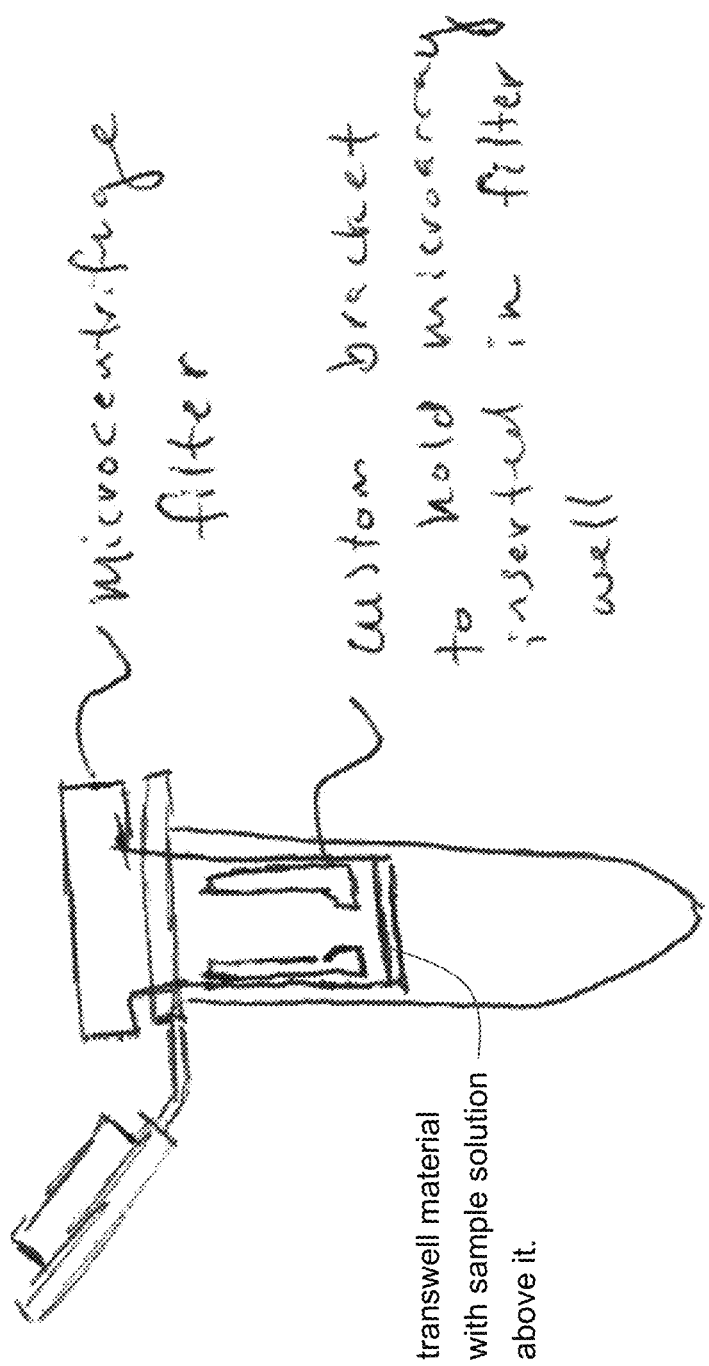

FIG. 7 is an embodiment of the DNA microarray positioned inside a microcentrifuge filter apparatus for the incubation process. In the figure the DNA microarray is constructed (similar to FIG. 1A) on a substrate that is small enough to fit inside of a standard microcentrifuge tube (e.g., a 1.5 ml Eppendorf tube). The DNA microarray is placed inside a microcentrifuge filter (FIGS. 8A, 8B and 9), which is placed inside the microcentrifuge tube (FIG. 9). Such microcentrifuge filters are known to those of skill in the art and are also commercially available. The filters can comprise any suitable material such as fiberglass, and further comprise a specific pore size suitable for separating unhybridized sample from the hybridized target. A hydrophobic membrane with a large pore size would keep the fluid stable above the membrane but still allow for elution of the entire sample after the incubation period and spin-down. Adhesion/adsorption tests will determine the best membrane material. The microcentrifuge filter can comprise an insert that holds the mini-microarray and reduces the interior space of the filter. Such an insert can be made out of any suitable inert/non-reactive material such as a plastic.

The target sample is then added to the well of the microcentrifuge filter to allow for incubation with the DNA microarray. Following the incubation period, the entire apparatus is loaded into a centrifuge and centrifugal force is used to draw the unhybridized sample away from the microarray, through the microcentrifuge filter, and into the base/bottom of the microcentrifuge tube where it can be collected for downstream processing. Unhybridized sample may also be collected on the surface of the microcentrifuge filter if the filter pore size is of suitable size. The DNA microarray is finally removed from the microcentrifuge tube for analysis.

The DNA mini-microarray with a sealed microfluidic well (the microcentrifuge filter apparatus) or the mini-microarray itself can be fit into a custom-made adapter/bracket (molded or 3D-printed) which allows the filter holding the mini-microarray, or the mini-microarray itself, to be snugly/securely fit into a cylindrical microcentrifuge filter (FIG. 9). Following the hybridization incubation period, the entire microcentrifuge tube is loaded into a centrifuge and centrifugal force is used to draw the unhybridized sample out of the sealed DNA microarray, through the microcentrifuge tube and, if present, through the filter, and into the base of the microcentrifuge tube where it can be collected for downstream processing. The DNA microarray is removed from the microcentrifuge tube for analysis.

In all of the embodiments, the mini-microarray assembly/apparatus is compact, requires a small sample volume, and enables collection of unused sample following the incubation period. The embodiments of FIGS. 3A-3D and 5A-5D will enable real-time optical readout to identify DNA hybridization on the array. The only required equipment for this readout is a microscope, camera, and computer. One embodiment of the present invention (FIGS. 6, 7 and 9) requires that the microarray to be removed from the microcentrifuge tube following the incubation period to optically assess DNA hybridization.

FIGS. 10A, 10B and 10C illustrate a hybridization assay using the mini-microarray assembly of the present invention. The mini-microarray glass slide with a gasket 10G (FIG. 10A) is lowered into the tube with the outlet port (in this case a funnel shape) toward the bottom of the tube. The centrifuge tube 30_1 is modified with an adapter/bracket to securely hold the mini-microarray assembly in place.

Sample solution, i.e., target oligonucleotides, in solution, is added to the tube. The lid L is closed and the centrifuge tube with lid closed (30_2) is incubated with agitation, typically in the horizontal position as in FIG. 10B (although incubation in the vertical position is also an option). Another possibility for mixing/incubation could be ultrasonic excitation of the tube. In some implementations, electrophoretic forces can be used to bring the target sample closer to the surface of the microarray. This would require the integration of electrodes into the microfluidic device.

Following the incubation period, the entire apparatus is loaded into a centrifuge and centrifugal force is used to draw the unhybridized sample away from the microarray, through the exit port, and into the base of the centrifuge tube where it can be collected for downstream processing (FIG. 10C).

As shown in FIG. 10A in the vertical positioning, the tube is filled to completely submerge the probe area of the mini-microarray assembly with target sample solution. In the horizontal positioning, shown in FIG. 10B, only the top of the array assembly needs to be covered with the sample solution. Sections of the tube may be filled to reduce unnecessary volume, e.g., use of a filter insert or other insert that would convert the cylindrical section of the interior to a rectangular shape.

Vertically orienting the tube and allowing for partial coverage of the chip is best if one has a small number of probes. Preferably, the backside of the chip can also be used. For a full array of probes, one needs to cover the chip entirely and a thin film of sample with the tube in the horizontal position would be optimal.

There are advantages and disadvantages to both orientations of the tube. In the vertical orientation, more sample will be required, but the mixing of probe and target molecules will be more thorough during incubation reaction period. In the horizontal position, less sample is necessary with the accompanying risk of less than thorough mixing between the sample and the probe molecules.

Example 1: Fabrication of a Miniaturized DNA Microarray

Figure 12:
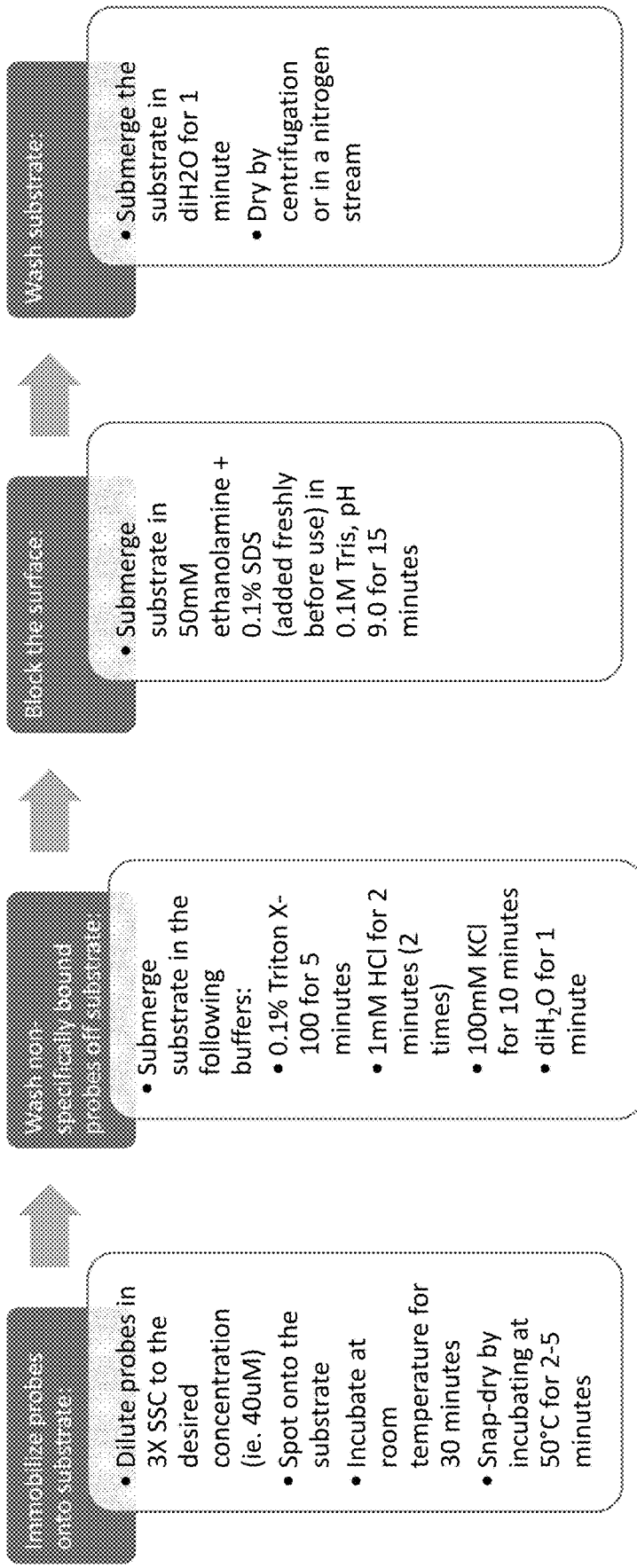
FIG. 12 shows a flow chart for a sample protocol for spotting oligonucleotides onto a substrate.
Figure 13B:
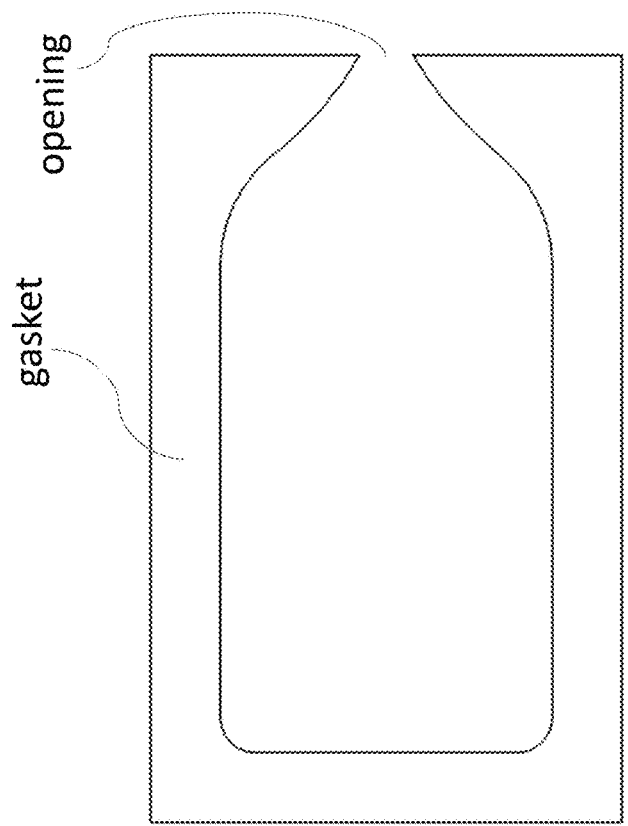
FIGS. 13A and 13B show a gasket (multiple views) that is plastic with double-sided adhesive on both sides; 11.0× 6.75 mm×0.12 mm with a 0.75 mm opening for elution of fluid.
Figure 13A:
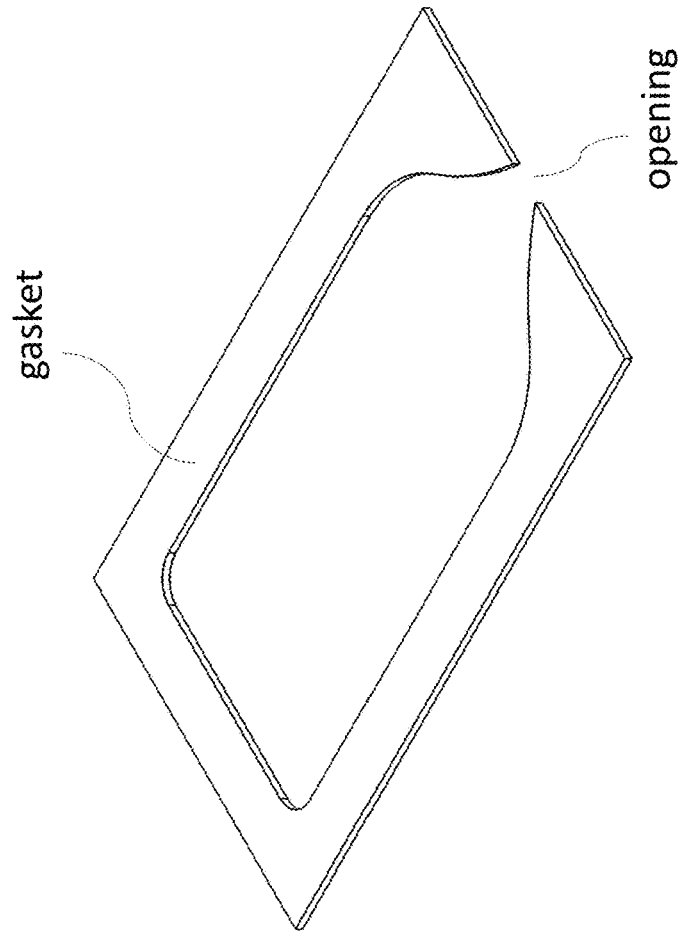
Figure 15B:
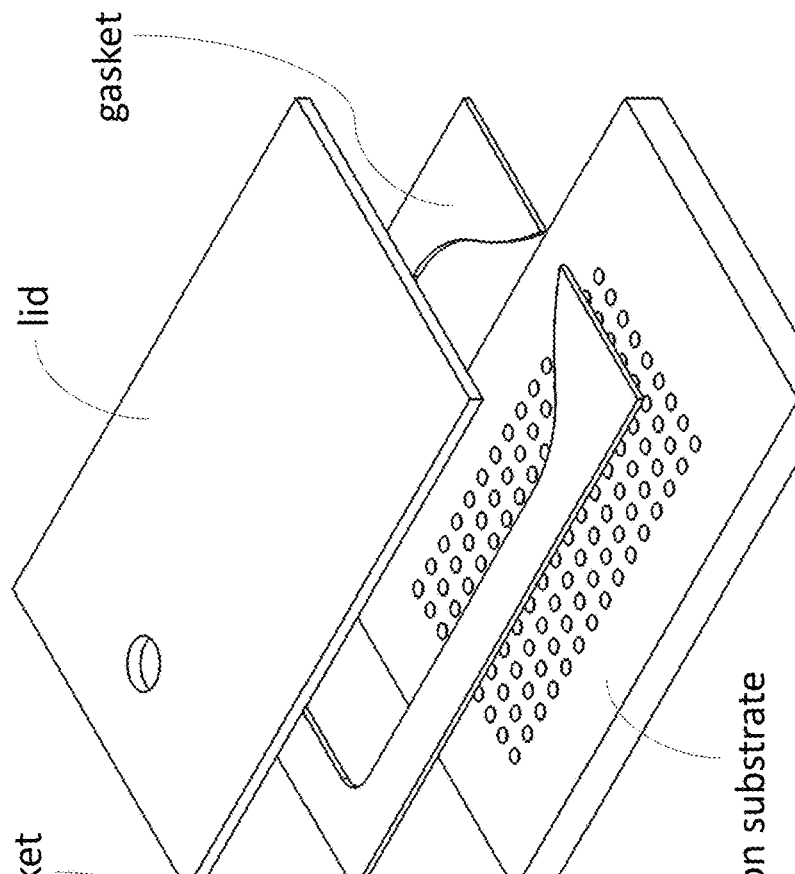
FIGS. 15A and 15B show an assembled hybridization well on a DNA array (exploded views).
Figure 15A:
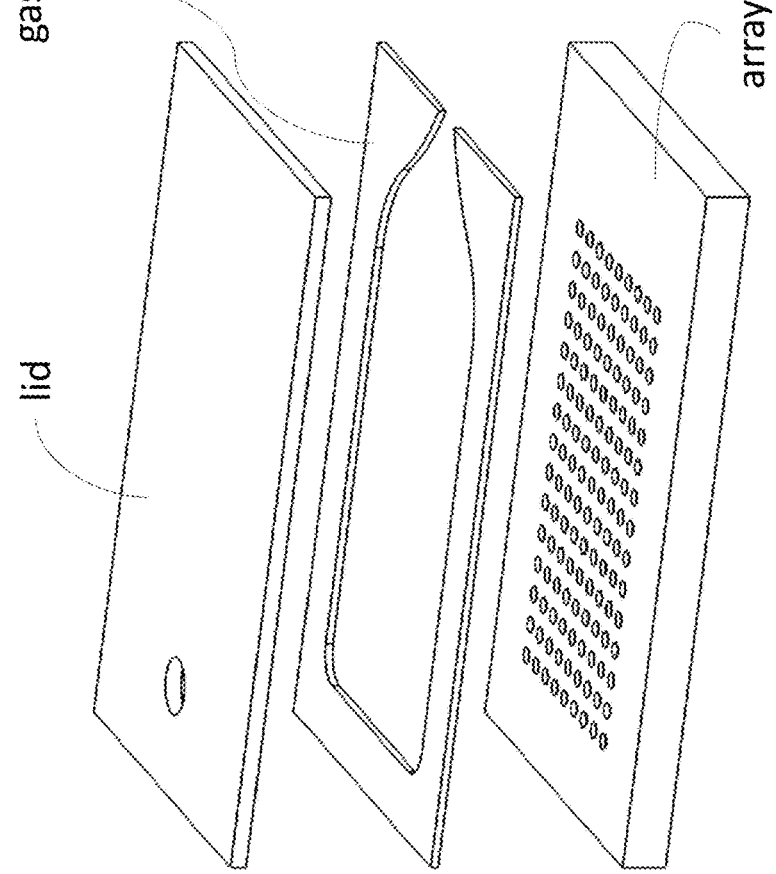
Figure 16A:
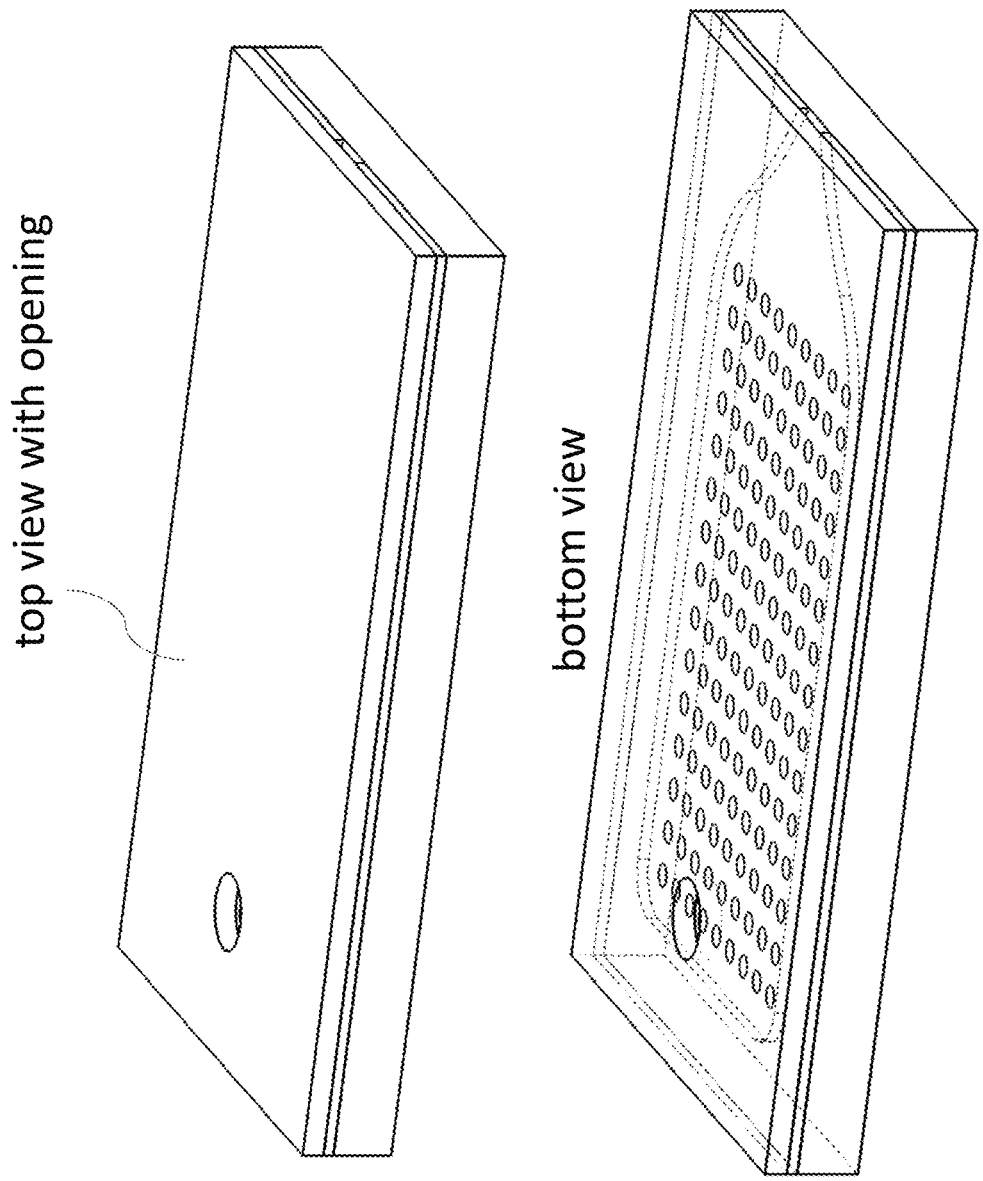
FIGS. 16A and 16B show an assembled hybridization well on a DNA array (multiple views).
Figure 16B:
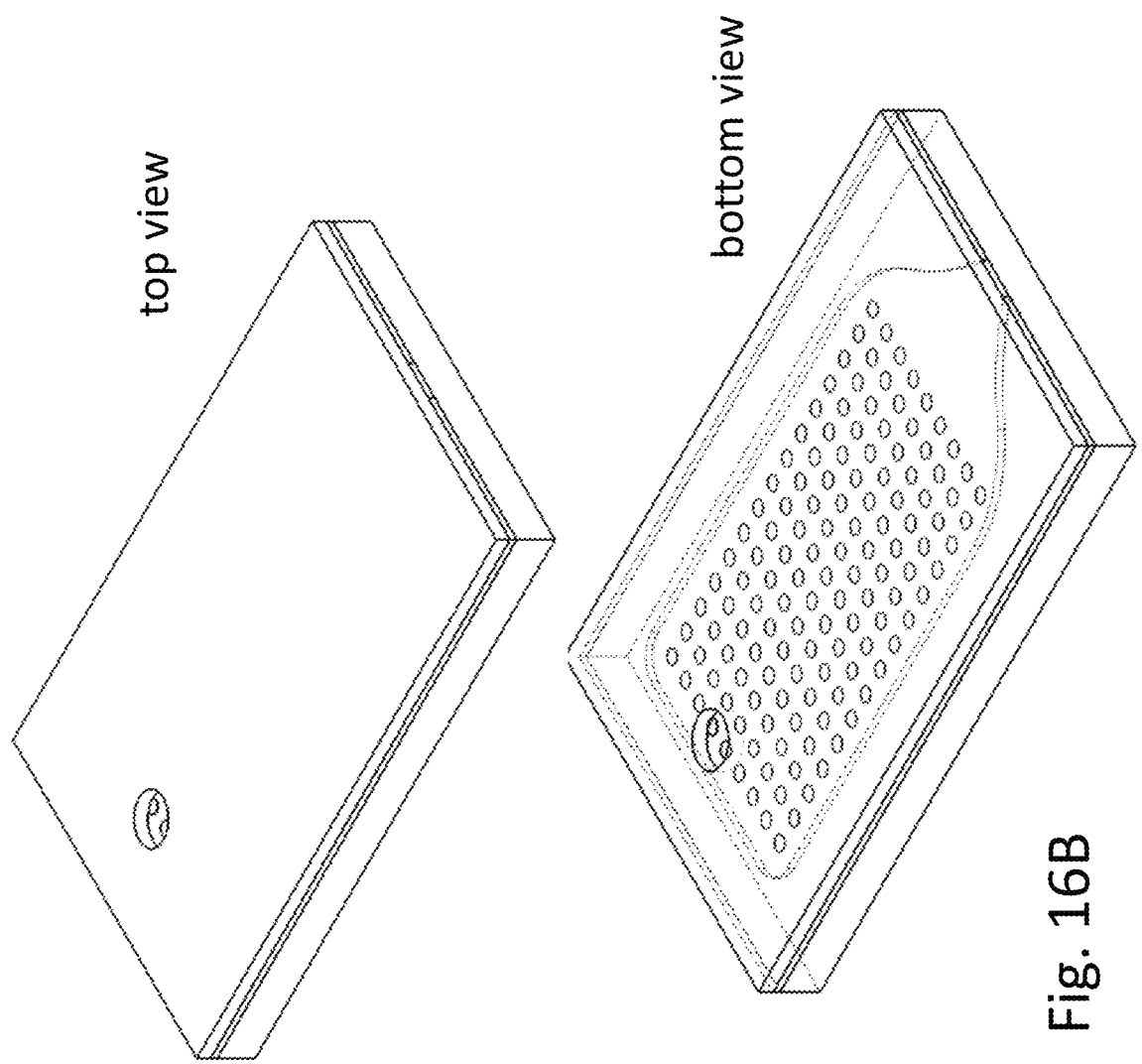
Figure 17C:
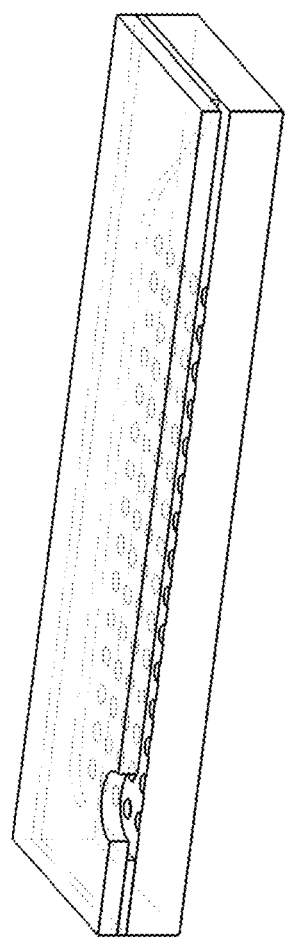
FIGS. 17 A-D show cross-section views of a hybridization well on a DNA array.
Figure 17D:
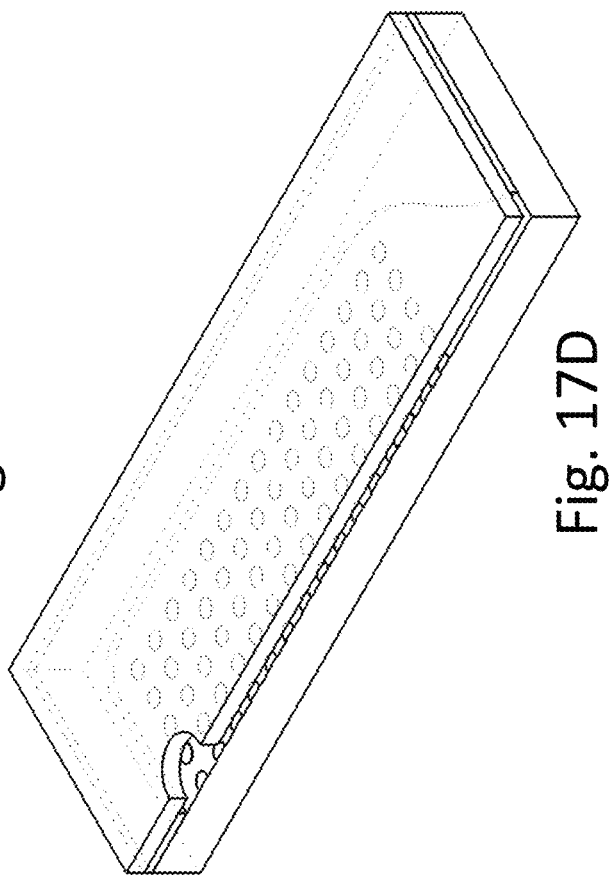
Figure 17A:
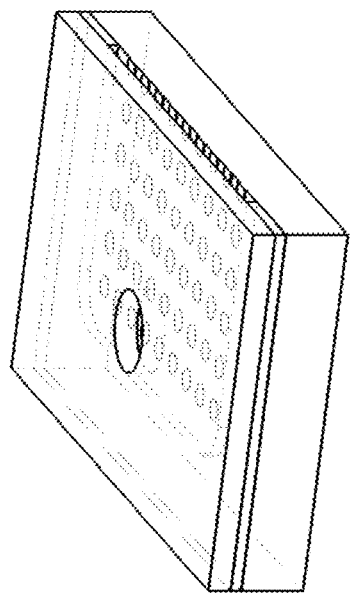
Figure 17B:
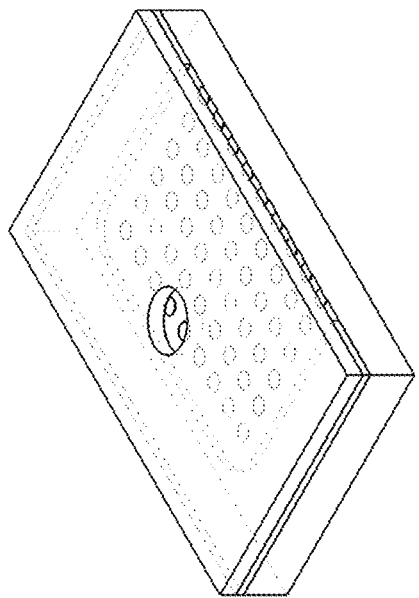
Figure 19:
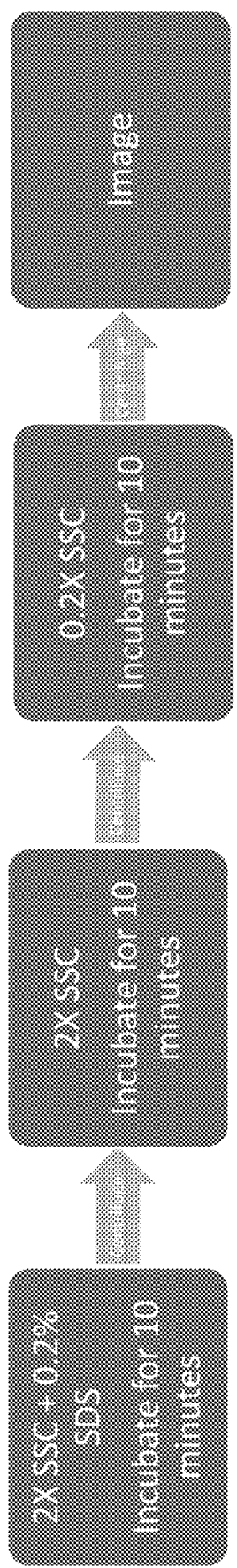
FIG. 19 shows a flow chart for post-hybridization washing steps.
Figure 20C:
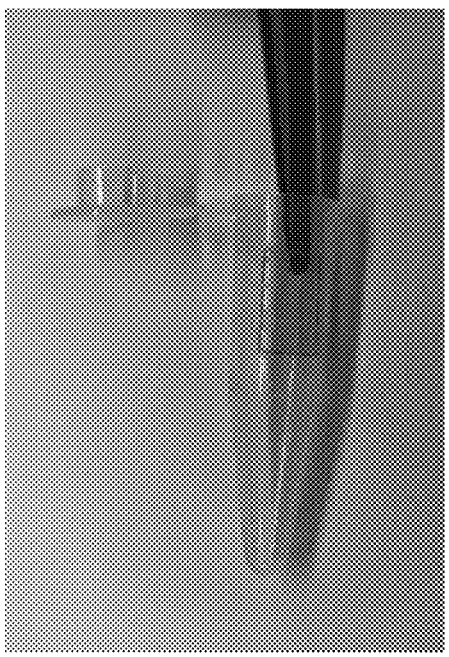
FIGS. 20 A-D show the steps of using a DNA microarray of the present invention. The device/apparatus (DNA microarray with custom hybridization chamber) is prepared, filled with 5.3 µl of sample, left in a humidity chamber for the duration of the hybridization process as determined for the specific hybridization assay, and then placed in a microcentrifuge tube to elute and collect the unused sample. Sample specifically hybridized to the probes of the DNA array can then be detected using standard means.
Figure 20D:
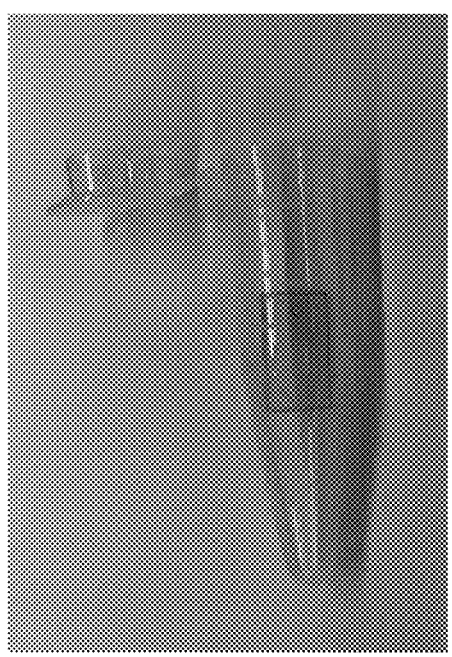
Figure 20B:
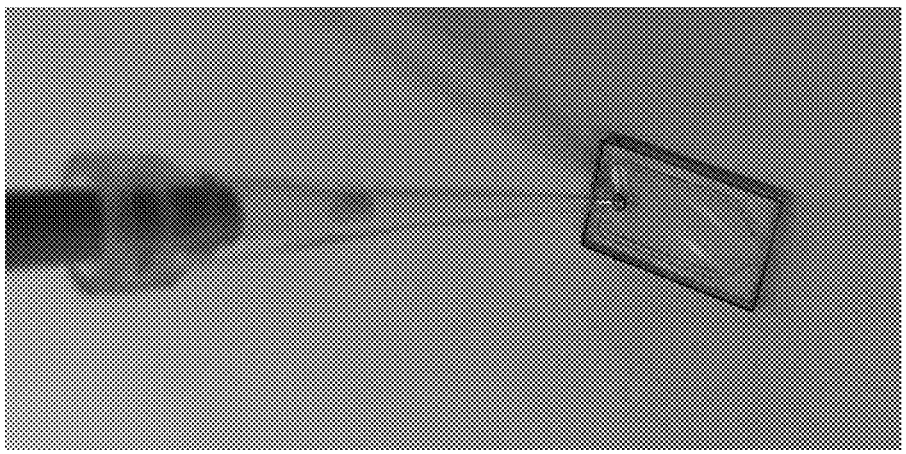
Figure 20A:
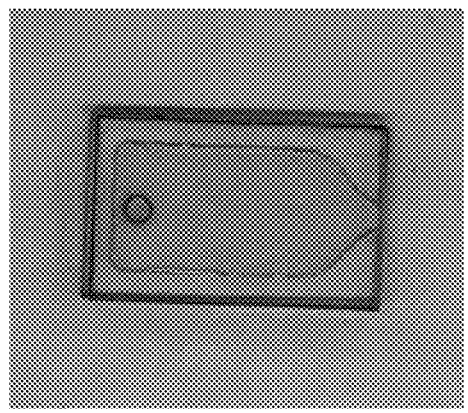

The microarray can be fabricated as described herein, although some variation can be incorporated into the fabrication procedure as known to those of skill in the art. In particular, the microarray is fabricated on 0.7 mm-thick glass substrates which are cut to dimensions of 11.0 mm in length and 6.75 mm in width. The substrates are treated with epoxysilane to create a surface to which amine-modified oligonucleotide probes can bind. (FIGS. 1A-B) The epoxysilane coating process proceeds as follows. First, the glass substrates are plasma treated with oxygen in a plasma asher (see for example, the Nordsom March plasma asher at nordson.com/en-us/divisions/march) for two minutes at 80 W power. The plasma-cleaned substrates are then immediately immersed in a freshly made solution of 2% (3-glycidyloxypropyl)trimethoxysilane in 95% ethanol and incubated for 16-18 hours at 37° C. with mixing. Following the incubation period, the substrates are removed from the solution and rinsed three times in pure ethanol. Finally, the substrates are dried in a stream of nitrogen and stored in a desiccator until ready for use. Once the substrates have been treated with epoxysilane, amine-modified oligonucleotide probes diluted in 3×SSC to a concentration of 40 uM are spotted on the surface. The probes are incubated at room temperature for 30 minutes followed by a snap-drying step at 50° C. for 2-5 minutes which allows for probe-substrate binding. The substrates can then be washed to remove any non-specifically bound probes by submerging them in a series of wash buffers which could include 0.1% Triton X-100, 1 mM HCl, 100 mM KCl, and diH$_2$O. The substrates are then blocked by submerging them in an ethanolamine solution which is made up of 0.1% SDS added freshly to 50 mM ethanolamine in 0.1 M Tris (pH 9.0). The substrates are incubated in the blocking buffer for 15 minutes at room temperature. Following the incubation period, the substrates are rinsed in deionized water and dried in a stream of nitrogen. The blocking step helps to reduce non-specific binding of analytes to the epoxysilane surface. All of the spotting, washing and blocking buffers and protocols are standard and known to those of skill in the art. For example, after the substrates are treated with epoxysilane, as described herein, the assay steps follow a protocol provided by one company that makes commercial epoxysilane slides (Schott Technical Glass Solutions, and the product is called Nexterion Epoxysilane Coating, or "Nexterion Slide E"). The protocol describes the steps starting from probe immobilization onto the epoxysilane surface (See FIG. 12) and continue through post-hybridization washes. (See FIG. 19). It is understood that variations of the protocol resulting in optimization of specific microarray assays can be determined by those skilled in the art.

Following the fabrication of the DNA microarray, a custom hybridization chamber is assembled and affixed to the array's surface. (FIGS. 13-17). The hybridization chamber is comprised of a piece of 120 micron-thick double-side-adhesive-backed plastic (SecureSeal Adhesive, Grace Bio-Labs, Bend, Oreg.) which is laser-cut to form a gasket, and a piece of about 250 micron-thick polycarbonate which is laser-cut to form a lid. The gasket has outer dimensions which match those of the microarray substrate and an inner rectangular cutout of dimension of about 9.0 mm in length and about 4.75 mm in width. There is also a cutout along one side of the gasket of dimension of about 0.75 mm, to allow for sample elution from the hybridization chamber. The polycarbonate lid has outer dimensions which match those of the microarray substrate and a single circular cutout of diameter of about 0.9 mm to allow for sample delivery to the hybridization chamber. The assembled hybridization chamber has an interior volume of about 5.3 microliters.

Figure 18C:
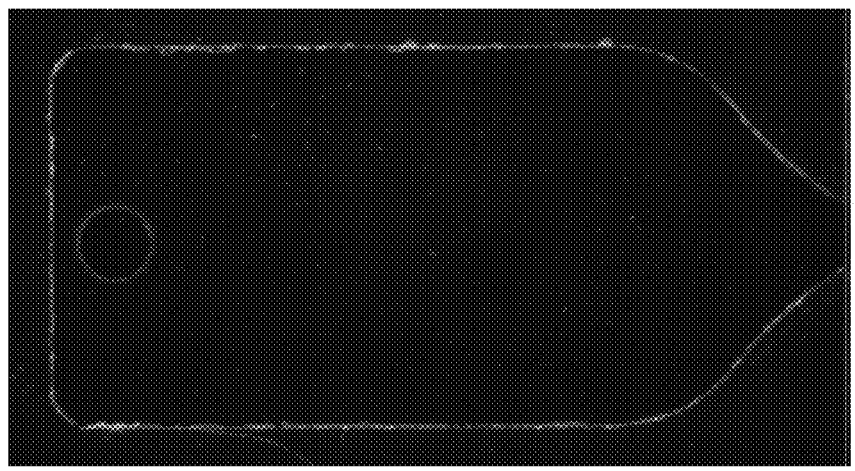
FIGS. 18 A-C show the steps of filling and emptying the hybridization well using a fluorescent sample. Sample recovery was about 98.7% (N=3) after spinning at 1000×g for 1 minute in a fixed rotor centrifuge.
Figure 18B:
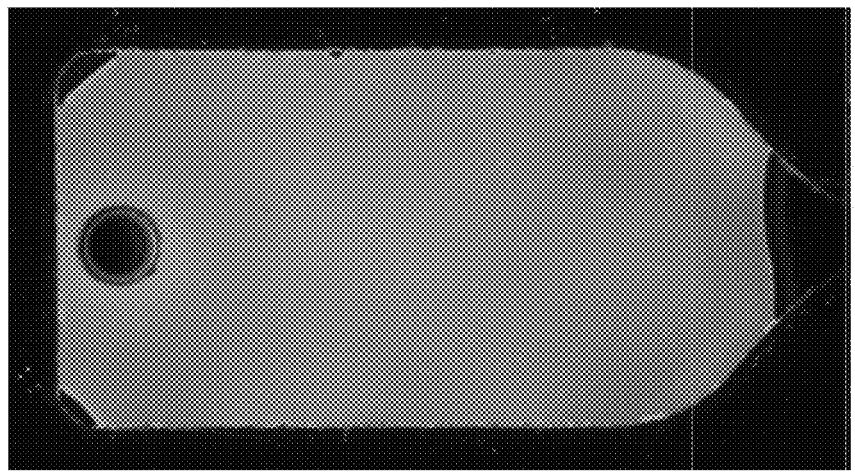
Figure 18A:
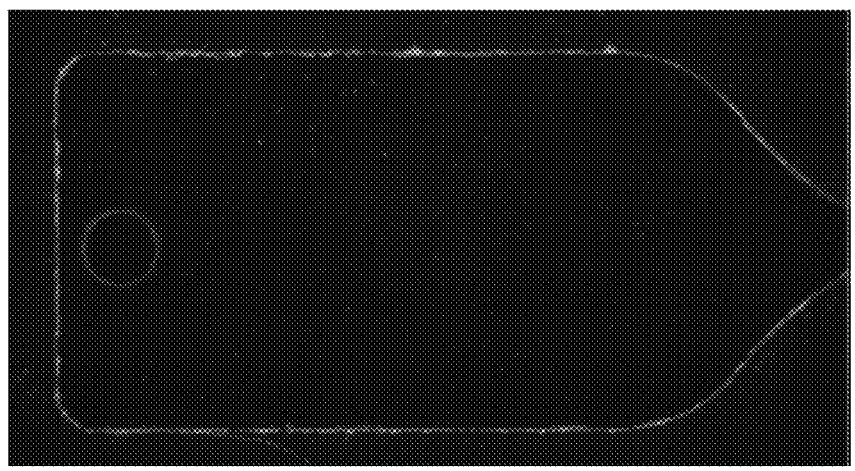

Once the custom hybridization chamber has been affixed to the DNA microarray, a sample may be added to the chamber. The sample is delivered by using a micropipette to dispense through the circular cutout in the lid of the chamber. The entire apparatus is then left to incubate in a humidity chamber for about 60 minutes at room temperature. Following the incubation period the apparatus is then placed into a standard microcentrifuge tube and spun in a centrifuge at 500×g for five minutes. The centrifugation process causes the sample to be eluted out of the cutout in the base of the gasket and it is collected at the bottom of the microcentrifuge tube. Initial tests using a sample of fluorescein diluted in water show a sample collection efficiency of 98.7% (n=3) (See FIGS. 18A-C).

Post-hybridization washing steps can then be performed in a similar fashion by pipetting the desired wash buffer (5.3 uL) into the inlet port, then placing the microarray into a microcentrifuge tube and spinning to remove the wash buffer. For example, a low stringency wash buffer such as 2×SSC+0.2% SDS can be used first, followed by increasing stringency wash buffers such as 2×SSC and 0.2×SSC (from Schott Slide E Protocol, see FIG. 19). After each wash buffer is added and incubated for 10 minutes at room temperature, the microarray is put into a microcentrifuge tube and spun at 500×g for 5 minutes in a tabletop centrifuge. This process may be repeated as necessary to remove unbound DNA. The microarray is then removed from the centrifuge tube and may be used for further downstream processing (e.g., imaging or sequencing). The recovered sample can be reused for additional analyses. Demonstration of the use of a DNA microarray as described herein is shown in FIGS. 20 A-D.

Example 2: DNA Hybridization Using the Mini Micro Array

Figures 21A, 21B:
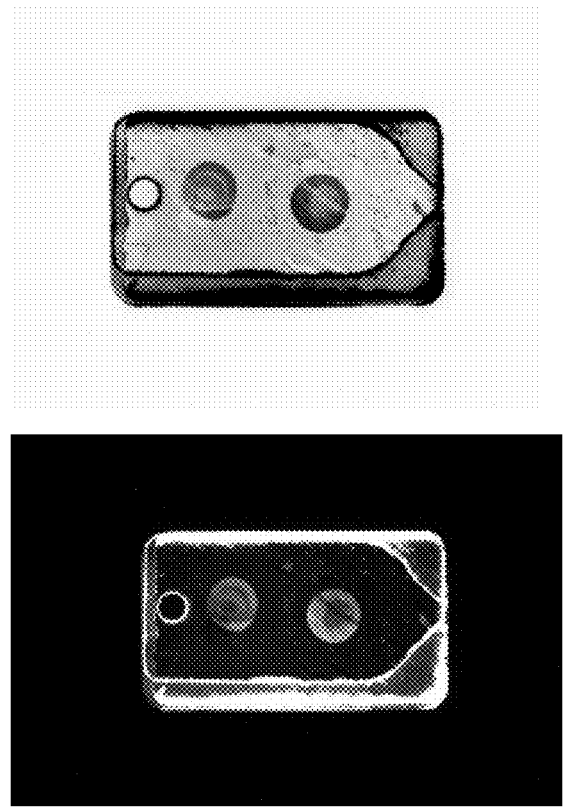
FIGS. 21 A-B show the results of a hybridization experiment using the claimed device. Fluorescently-labeled DNA is specifically bound to/hybridized with the oligonucleotide probes immobilized on the surface. Two fluorescent spots are visible on the surface of the glass substrate (FIG. 20 A and FIG. 20 B are the same image with coloring inverted.

In one example, the DNA which is hybridized to the probes on the array is fluorescently labeled with a 5' Alexa Fluor 488 fluorophore. The DNA may be visualized on the array using a fluorescence microscope. One such example is show in FIGS. 21 A-B. As shown in the figures, there are two identical probes on the array surface and fluorescently-labeled complementary DNA is hybridized to the probes. The locations of successful hybridization are imaged using a fluorescence imaging system. Such imagining systems are well known to those of skill in the art.

To enable ease of handling and imaging of the assembled microarrays, a custom fixture (chiplet) as shown in FIGS. 22 A-B was designed and constructed. The fixture has the same footprint as that of a 96-well plate, enabling compatibility with many standard laboratory instruments (e.g., microscopy stages). The fixture is comprised of two anodized aluminum plates and a rubber gasket. The plates have 36 rectangular cutouts in which assembled microarrays may be secured in place. Similar fixtures can be designed and constructed for various embodiments of the assembled microarrays as described herein.

While this invention has been particularly shown and described with references to preferred embodiments thereof, it will be understood by those skilled in the art that various changes in form and details may be made therein without departing from the scope of the invention encompassed by the appended claims.

What is claimed is:

1. A miniaturized DNA microarray assembly, consisting of:
   a) a single high-density array of oligonucleotide probes printed on a single solid substrate, wherein the dimensions of the solid substrate are about 14.0 mm by about 8 mm, or less;
   b) an inert enclosure surrounding sides and bottom of the single solid substrate, wherein the enclosure has a fluid inlet port and a fluid outlet/exit port which allows fluid to flow over and contact the oligonucleotide probes of the array; and
   c) an optically transparent top surface sealed to the enclosure.

2. The enclosure of claim 1, wherein the edge of one of the sides of the enclosure comprises a rupturable or break-away barrier.

3. The microarray assembly of claim 1, wherein the dimensions of the solid substrate of the array are about 11.0 mm by about 6.75 mm.

4. A method of assaying a sample for one, or more, nucleotide sequences of interest, the method comprising:
   a) contacting the sample with a miniaturized DNA microarray of claim 1, under conditions sufficient for the specific hybridization of the nucleotide sequences of interest; and
   b) detecting the presence, or absence of hybridization on the array, wherein detection of hybridization indicates the presence of the nucleotides of interest in the sample.

5. The microarray assembly of claim 1, wherein the dimensions of the solid substrate of the single array are about 11.0 mm by about 7.0 mm.

6. The microarray assembly of claim 1, wherein the density of the oligonucleotide probes printed on the solid substrate comprises about 30,000 to about 50,000 individual probes printed on the surface of the single solid substrate.

7. The method of claim 4, wherein the size of the sample to be assayed is about 100 µl to less than 10 µl.

* * * * *